United States Patent
Eckhardt

(10) Patent No.: US 8,809,361 B2
(45) Date of Patent: Aug. 19, 2014

(54) 2,3-DIHYDROFURO[2,3-C]PYRIDINES, THEIR USE AS MODULATORS OF THE G-PROTEIN-COUPLED RECEPTOR GPR119 AND PHARMACEUTICAL COMPOSITIONS THEREOF

(71) Applicant: Matthias Eckhardt, Biberach an der Riss (DE)

(72) Inventor: Matthias Eckhardt, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/887,887

(22) Filed: May 6, 2013

(65) Prior Publication Data

US 2013/0296354 A1    Nov. 7, 2013

(30) Foreign Application Priority Data

May 7, 2012   (EP) .................................... 12166992

(51) Int. Cl.
*C07D 491/20* (2006.01)
*A61K 31/438* (2006.01)

(52) U.S. Cl.
CPC ............ *C07D 491/20* (2013.01); *A61K 31/438* (2013.01)
USPC .......................................... 514/278; 546/18

(58) Field of Classification Search
CPC ............................ A61K 31/438; C07D 491/20
USPC ...................................... 546/18, 278
See application file for complete search history.

(56) References Cited

FOREIGN PATENT DOCUMENTS

WO       2011140161  A1    11/2011

OTHER PUBLICATIONS

International Search Report for PCT/EP2013/059346 mailed Jun. 25, 2013.
Jones, Robert M. "GPR119 agonists for the treatment of type 2 diabetes" (2009) Expert Opin. Ther. Patents 19(10) pp. 1339-1359.
Zhu, Xiaoyun et al. "The first pharmacophore model for potent G protein-coupled receptor 119 agonist" European Journal of Medicinal Chemistry 46 (2011) pp. 2901-2907.

*Primary Examiner* — Rita Desai
(74) *Attorney, Agent, or Firm* — Michael P. Morris; Timothy X. Witkowski

(57) ABSTRACT

The present invention relates to compounds of general formula I,

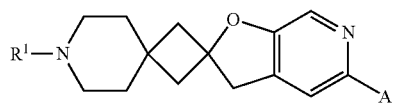

wherein the groups $R^1$ and A are as defined in the application, which have valuable pharmacological properties, and in particular bind to the GPR119 receptor and modulate its activity.

10 Claims, No Drawings

2,3-DIHYDROFURO[2,3-C]PYRIDINES, THEIR USE AS MODULATORS OF THE G-PROTEIN-COUPLED RECEPTOR GPR119 AND PHARMACEUTICAL COMPOSITIONS THEREOF

This application claims priority to European Patent Application No. 12 166 992.3, filed May 7, 2012, the contents of which are hereby incorporated by reference in its entirety.

FIELD OF THE INVENTION

The present invention relates to new compounds of formula I

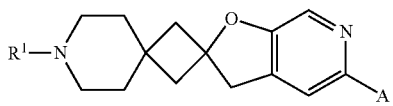

wherein the groups $R^1$ and A are defined as hereinafter, to processes for preparing such compounds, to their use as modulators of the G-protein-coupled receptor GPR119, to methods for their therapeutic use, in particular in diseases and conditions mediated by the modulation of the G-protein-coupled receptor GPR119, and to pharmaceutical compositions comprising them.

BACKGROUND OF THE INVENTION

Diabetes mellitus is a serious metabolic disease which affects more than 100 million people worldwide. In the USA there are more than 12 million diabetics with 600,000 new cases diagnosed every year. The prevalence of diabetes mellitus is increasing, resulting in a high frequency of complications and a substantial impairment of quality of life and life expectancy. Because of diabetes-associated microvascular complications, in the industrialised countries type 2 diabetes is currently the most common cause of adult-onset loss of vision, renal insufficiency and amputations. In addition, type 2 diabetes is associated with a two- to five-fold increase in the risk of cardiovascular disease.

The UKPDS study (United Kingdom Prospective Diabetes Study) showed that intensive treatment with common therapeutic agents, e.g. metformin, sulphonylureas or insulin, results in only a limited improvement in glycaemic control (difference in the HbA1c value~0.9%). Moreover, glycaemic control deteriorated considerably over time even in patients in the intensive treatment group, and this was put down to a deterioration in beta cell function. Diabetes is also a major cause of damage to the retina at the back of the eye and increases the risk of cataract and glaucoma. Finally, diabetes is associated with nerve damage, particularly in the legs and feet, which affects the patient's ability to feel pain and contributes to serious infections. All in all, complications of diabetes are one of the major causes of death worldwide.

Adiposity (obesity) is the result of an imbalance between calorie intake and energy consumption. It correlates to a high degree with insulin resistance and diabetes. However, the molecular mechanisms that are involved in obesity/diabetes syndromes are not yet clear. At an early stage of the development of obesity, an increased insulin secretion balances out the insulin resistance and protects the patient from hypergly-caemia. However, after a time, the beta cell function worsens and non-insulin-dependent diabetes develops in about 20% of the obese population. Obesity has thus become a critical risk factor for diabetes, but the factors that predispose one group of patients to a pathological change in insulin secretion as a response to the accumulation of fat are currently unknown. Obesity also significantly increases the risk of the development of cardiovascular disease. Diabetes is also implicated in the formation of kidney complaints, eye complaints and problems of the nervous system. Kidney disease, also known as nephropathy, sets in when the filtering mechanism of the kidneys is disrupted and proteins escape into the urine in excessive amounts and finally the kidney fails. Therefore there is a medical need for medicaments for preventing and/or treating metabolic disorders (particularly diabetes, predominantly type 2 diabetes) and the complications thereof. In particular there is a need for medicaments with good activity in terms of glycaemic control, disease-modifying properties and reducing cardiovascular morbidity and mortality, and which also have a better safety profile.

Dyslipidemia is a disorder of lipoprotein metabolism, including lipoprotein overproduction or deficiency. Dyslipidemias may be manifested by elevation of the total cholesterol, LDL cholesterol and triglyceride and free fatty acid concentrations, and a decrease in high-density lipoprotein (HDL) cholesterol concentration in the blood. Dyslipidemia occurs often in situations including diabetes, a common cause of lipidemia. For adults with diabetes, it has been recommended that the levels of LDL, HDL, and total cholesterol, and triglyceride be measured every year. Optimal LDL cholesterol levels for adults with diabetes are less than 100 mg/dL (2.60 mmol/L), optimal HDL cholesterol levels are equal to or greater than 40 mg/dL (1.02 mmol/L), and desirable triglyceride levels are less than 150 mg/dL (1.7 mmol/L).

GPR119 is a G-protein coupled receptor (also known as GPCR2, RUP3, SNORF25 or GDIR) which is expressed predominantly in the beta cells of the pancreas and in the K- and L-cells of the intestine. The GPR119 receptor and isoforms have been identified in mammalian species including human, rat, mouse, hamster, chimpanzee, rhesus monkey, cattle and dog. The expression of GPR119 in the pancreas and particularly in the pancreatic β-cells led to the hypothesis that the GPR119 receptor could have effects upon insulin secretion. Activation of the receptor stimulates the cAMP signal pathway, increasing the intracellular levels of cAMP in these cells. This will lead to an improved diabetic situation by a dual action of such a compound: stimulation of cAMP in the beta cell occurs directly via activation of GPR119 in these cells and furthermore indirectly via stimulation of the release of neuroendocrine peptides like GIP and GLP-1 and PYY from the gut. The release of these peptides may have also additional beneficial effects, e.g. on food intake, gastric emptying and other yet unknown functions. Also, a GPR119 agonist can be expected to bring about an improvement in the beta cell function and the beta cell mass. In fact, activation of GPR119 stimulates insulin secretion in-vitro and in-vivo (in rodents) in a glucose-dependent manner. The discovery of two endogenous ligands, lysophospha-tidylcholine (LPC) and oleoylethanolamide (OEA) as well as more potent GPR119 agonists have led to the characterization of GPR119 as both an insulin and incretin (GLP-1 and GIP) secretagogue receptor capable of lowering plasma glucose and thereby facilitating glycemic control without the risk of hypoglycemia (Biochem. Biophys. Res. Comm. 2005, 744-751; Cell Metabolism 2006, 167-175; Endocrinolgy 2007, 2601-9). It has recently been shown that GPR119 agonists effectively lower the blood glucose levels in diabetic rodents without the risk of hypoglycaemia. GPR119 knockout animals have shown that both insulin and incretin secretion induced by GPR119 agonists are dependent upon GPR119 receptor. In addition, it has been shown that GPR119 agonists decrease food intake resulting in weight loss in Sprague Dawley rats. Therefore the GPR119 agonists may be expected to have a therapeutic benefit in metabolic diseases. Examples of such diseases include type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction and bone-related diseases (such as osteoporosis, rheumatoid arthritis or osteoarthritis). For comparison and additional information also see 1. Dhayal, S., Morgan, N. G. The significance of GPR119 agonists as a future treatment for type 2 diabetes. Drug News Perspect. 2010, 23(7), 418-24.
2. Yoshida, S., Tanaka, H., Oshima, H., Yamazaki, T., Yonetoku, Y., Ohishi, T., Matsui, T., Shibasaki, M. AS1907417, a novel GPR119 agonist, as an insulinotropic and β-cell preservative agent for the treatment of type 2 diabetes. Biochem Biophys Res Commun. 2010, 400(4), 745-51.
3. Jones, R. M., Leonard, J. N., Buzard, D. J., Lehman, J. GPR119 agonists for the treatment of type 2 diabetes. Expert Opinion on Therapeutic Patents 2009, Vol. 19, No. 10: 1339-1359.

AIM OF THE PRESENT INVENTION

The aim of the present invention is to provide new compounds, in particular new 2,3-dihydro-furo[2,3-c]pyridine derivatives, which are active with regard to the G-protein-coupled receptor GPR119.

Another aim of the present invention is to provide new compounds, in particular new 2,3-dihydro-furo[2,3-c]pyridine derivatives, which are agonists of the G-protein-coupled receptor GPR119.

A further aim of the present invention is to provide new compounds, in particular new 2,3-dihydro-furo[2,3-c]pyridine derivatives, which have an activating effect on the G-protein-coupled receptor GPR119 in vitro and/or in vivo and possess suitable pharmacological and pharmacokinetic properties to use them as medicaments.

A further aim of the present invention is to provide effective GPR119 agonists, in particular for the treatment of metabolic disorders, for example diabetes, dyslipidemia and/or obesity.

A further aim of the present invention is to provide methods for treating a disease or condition mediated by the activation the G-protein-coupled receptor GPR119 in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular 2,3-dihydro-furo[2,3-c]pyridine derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

OBJECT OF THE INVENTION

It has now been found that the compounds according to the invention described in more detail hereinafter have surprising and particularly advantageous properties, and in particular as GPR119 agonists.

In a first aspect the invention thus relates to a compound of formula I

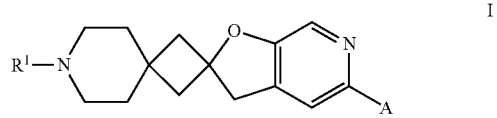

wherein
$R^1$ is selected from the group $R^1$-G1 consisting of
  a) a 5- or 6-membered heteroaromatic ring containing 1, 2, or 3 heteroatoms independently of each other selected from N, O, and S, which may be optionally substituted with a group $R^C$ and/or one or more substituents independently selected from $L^A$; and
  b) a group —C(=O)—O—$R^a$, wherein $R^a$ denotes $C_{1-6}$-alkyl optionally mono- or polysubstituted with fluorine, or $C_{3-6}$-cycloalkyl optionally mono- or polysubstituted with fluorine and optionally substituted with a group selected from $CH_3$, $CF_3$, and $CHF_2$; and
  c) a group —$CH_2$—$R^b$, wherein $R^b$ denotes $C_{1-6}$-alkyl optionally mono- or polysubstituted with fluorine, or $C_{3-6}$-cycloalkyl optionally mono- or polysubstituted with fluorine and optionally substituted with a group selected from $CH_3$, $CF_3$, and $CHF_2$; and
A is selected from the group A-G1 consisting of
  a) piperidin-4-yl, 1,2,3,6-tetrahydropyridin-4-yl, 5-methyl-1,2,3,6-tetrahydropyridin-4-yl, and piperazin-1-yl, each of which is substituted at the N with a $C_{1-4}$-alkyl-S(=O)$_2$— group; and
  b) a phenyl ring and a 6-membered heteroaromatic ring containing 1 or 2 N, each of which may be substituted with a group T and may be optionally substituted with one or more substituents independently selected from $L^A$;
T is selected from the group T-G1 consisting of F, Cl, Br, I, CN, OH, $NO_2$, $C_{1-6}$-alkyl-, $C_{1-6}$-alkenyl-, $C_{1-6}$-alkynyl-, $C_{3-6}$-cycloalkyl, $C_{1-6}$-alkyl-O—, $C_{3-6}$-cycloalkyl-O—, $C_{1-6}$-alkyl-S—, HO—C(=O)—, $C_{1-6}$-alkyl-O—C(=O)—, $C_{1-4}$-alkyl-C(=O)—, $C_{3-6}$-cycloalkyl-C(=O)—, $C_{1-4}$-alkyl-S(=O)—, $C_{1-4}$-alkyl-S(=O)$_2$—, $R^{NT1}R^{NT2}$N—, $R^{NT1}R^{NT2}$N—C(=O)—, $R^{NT1}R^{NT2}$N—S(=O)$_2$—, $R^{NT1}R^{NT2}$N—C(=O)—($R^N$)N—, heterocyclyl, heterocyclyl-O—, aryl, aryl-O—, heteroaryl and heteroaryl-O—,
  wherein each alkyl, alkenyl, alkynyl, and cycloalkyl group may be optionally substituted with one or more substituents independently of each other selected from F, Cl, CN, OH, $C_{1-3}$-alkyl, $C_{3-6}$-cycloalkyl, $C_{1-3}$-alkyl-O—, $R^{NT1}R^{NT2}$N—, $R^{NT1}R^{NT2}$N—C(=O)—, $C_{1-4}$-alkyl-S(=O)—, $C_{1-4}$-alkyl-S(=O)$_2$—, $R^{NT1}R^{NT2}$N—S(=O)$_2$—, aryl, heteroaryl, and heterocyclyl, and
  wherein aryl denotes phenyl or naphthyl, and
  wherein heteroaryl is a 5- or 6-membered aromatic ring which contains 1, 2, 3 or 4 heteroatoms independently of each other selected from N, O and S, wherein the H-atom in one or more NH groups may be optionally replaced by $R^N$; and wherein heterocyclyl is a 4- to 7-membered unsaturated or saturated carbocyclic ring in which 1, 2 or 3 —CH$_2$- groups independently of each other are replaced by NR$^N$, O, —C(=O)—, S, —S(=O)— or —S(=O)$_2$—, and/or in which a —CH< group is replaced by N; and wherein each aryl, heteroaryl or heterocyclyl group may be optionally substituted with one or more substituents independently of each other selected from L$^A$; and R$^N$ independently of each other is selected from the group R$^N$-G1 consisting of H, C$_{1-4}$-alkyl, C$_{1-4}$-alkyl-C(=O)—, and C$_{1-4}$-alkyl-S(=O)$_2$—; and R$^{NT1}$ is selected from the group R$^{NT1}$-G1 consisting of H, C$_{1-6}$-alkyl, C$_{3-6}$-cycloalkyl, C$_{1-6}$-alkyl-C(=O)—, C$_{1-6}$-alkyl-S(=O)$_2$, heterocyclyl, aryl and heteroaryl, wherein each alkyl and cycloalkyl group may be optionally substituted with one or more substituents independently of each other selected from the group consisting of F, OH, CN, C$_{1-4}$-alkyl, C$_{1-4}$-alkyl-O—, R$^N{}_2$N, C$_{1-4}$-alkyl-S(=O)$_2$—, C$_{3-6}$-cycloalkyl, heterocyclyl, phenyl and heteroaryl; and wherein heterocyclyl may be optionally substituted with one or more substituents independently of each other selected from F, C$_{1-4}$-alkyl, R$^N{}_2$N, OH and C$_{1-4}$-alkyl-O—; and wherein heterocyclyl is a C$_{4-7}$-cycloalkyl ring in which 1 or 2-CH$_2$-groups independently of each other are replaced by NR$^N$, O, C(=O), S, S(=O) or S(=O)$_2$; and wherein aryl is phenyl or naphthyl; and wherein heteroaryl is a 5- or 6-membered aromatic ring which contains 1, 2 or 3 heteroatoms independently of each other selected from N, O and S, wherein the H-atom in one or more NH groups may be optionally replaced by R$^N$; and wherein aryl and heteroaryl may be optionally substituted with one or more substituents L$^A$; and R$^{NT2}$ is selected from the group R$^{NT2}$-G1 consisting of H and C$_{1-6}$-alkyl; or R$^{NT1}$ and R$^{NT2}$ are linked to form one group selected from the group R$^{NT1}$R$^{NT2}$-G1 consisting of a C$_{3-5}$-alkylene group, wherein 1 or 2 —CH$_2$-groups independently of each other are replaced by NR$^N$, O, C(=O), S, S(=O) or S(=O)$_2$; and which may be optionally substituted with one or more substituents independently of each other selected from F, C$_{1-4}$-alkyl, (R$^N$)$_2$N, OH and C$_{1-4}$-alkyl-O—;

L$^A$ is selected from the group L$^A$-G1 consisting of F, Cl, Br, CN, OH, NO$_2$, C$_{1-4}$-alkyl-, C$_{1-4}$-alkyl-O—, (R$^N$)$_2$N—C(=O), (R$^N$)$_2$N—, and C$_{1-4}$-alkyl-S(=O)$_2$—, wherein each alkyl group may be optionally substituted with one or more substituents independently of each other selected from F, Cl, CN, OH and C$_{1-3}$-alkyl-O—; and R$^C$ is selected from the group R$^C$-G1 consisting of F, Cl, Br, I, CN, OH, NO$_2$, C$_{1-6}$-alkyl-, C$_{2-6}$-alkenyl-, C$_{2-6}$-alkynyl-, C$_{3-6}$-cycloalkyl, C$_{1-6}$-alkyl-O—, C$_{3-6}$-cycloalkyl-O—, C$_{1-6}$-alkyl-S—, HO—C(=O)—, C$_{1-6}$-alkyl-O—C(=O)—, C$_{1-4}$-alkyl-C(=O)—, C$_{3-6}$-cycloalkyl-C(=O)—, C$_{1-4}$-alkyl-S(=O)—, C$_{1-4}$-alkyl-S(=O)$_2$—, R$^{NT1}$R$^{NT2}$N—, R$^{NT1}$R$^{NT2}$N—C(=O)—, R$^{NT1}$R$^{NT2}$N—S(=O)$_2$—, R$^{NT1}$R$^{NT2}$N—C(=O)—(R$^N$)N—, heterocyclyl, heterocyclyl-O—, aryl, aryl-O—, heteroaryl and heteroaryl-O—, wherein each alkyl, alkenyl, alkynyl, and cycloalkyl group may be optionally substituted with one or more substituents independently of each other selected from F, Cl, CN, OH, C$_{1-3}$-alkyl, C$_{3-6}$-cycloalkyl, C$_{1-3}$-alkyl-O—, R$^{NT1}$R$^{NT2}$N—, R$^{NT1}$R$^{NT2}$N—C(=O)—, C$_{1-4}$-alkyl-S(=O)—, C$_{1-4}$-alkyl-S(=O)$_2$—, R$^{NT1}$R$^{NT2}$N—S(=O)$_2$—, aryl, heteroaryl, and heterocyclyl, and wherein aryl denotes phenyl or naphthyl, and wherein heteroaryl is a 5- or 6-membered aromatic ring which contains 1, 2, 3, or 4 heteroatoms independently of each other selected from N, O and S, wherein the H-atom in one or more NH groups may be optionally replaced by R$^N$; and wherein heterocyclyl is a 4- to 7-membered unsaturated or saturated carbocyclic ring in which 1, 2 or 3 —CH$_2$- groups independently of each other are replaced by NR$^N$, O, —C(=O)—, S, —S(=O)— or —S(=O)$_2$—, and/or in which a —CH-group is replaced by N; and wherein each aryl, heteroaryl or heterocyclyl group may be optionally substituted with one or more substituents independently of each other selected from LA;

including any tautomers and stereoisomers thereof,
or a salt thereof
or a solvate or hydrate thereof.

In a further aspect the present invention relates to processes for preparing a compound of general formula I and to new intermediate compounds in these processes.

A further aspect of the invention relates to a salt of the compounds of general formula I according to this invention, in particular to a pharmaceutically acceptable salt thereof.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are mediated by activating the G-protein-coupled receptor GPR119 in a patient in need thereof characterized in that a compound of general formula I or a pharmaceutically acceptable salt thereof is administered to the patient.

According to another aspect of the invention, there is provided a method for treating a metabolic disease or disorder in a patient in need thereof characterized in that a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition mediated by the activation of the G-protein-coupled receptor GPR119 in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to a use of a compound of the general formula I or a pharmaceutically acceptable salt thereof in combination with one or more additional therapeutic agents for the treatment of diseases or conditions which are mediated by the activation of the G-protein-coupled receptor GPR119.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly A, $R^1$, T, $R^N$, $R^{NT1}$, $R^{NT2}$, $L^A$, and $R^C$ are defined as above and hereinafter. If residues, substituents, or groups occur several times in a compound, as for example $R^N$ and $L^A$, they may have the same or different meanings. Some preferred meanings of individual groups and substituents of the compounds according to the invention will be given hereinafter. Any and each of these definitions may be combined with each other.

$R^1$:

$R^1$-G1:

The group $R^1$ is preferably selected from the group $R^1$-G1 as defined hereinbefore and hereinafter.

$R^1$-G2:

According to one embodiment the group $R^1$ is selected from the group $R^1$-G2 consisting of a)

[chemical structures]

wherein each group may be optionally substituted with one substituent $L^A$ and one substituent $R^C$; and b)

[chemical structures]

wherein each alkyl residue may be substituted with 1 to 3 F atoms; and c)

[chemical structures]

$R^1$-G2a:

According to one embodiment the group $R^1$ is selected from the group $R^1$-G2a consisting of

[chemical structures]

wherein each group may be optionally substituted with one substituent $L^A$ and one substituent $R^C$.

$R^1$-G3:

In another embodiment the group $R^1$ is selected from the group $R^1$-G3 consisting of a)

[chemical structures]

wherein each ring may be substituted with one substituent $R^C$; and b)

[chemical structures]

wherein each alkyl residue may be substituted with 1 to 3 F atoms; and c)

[chemical structures]

R$^1$-G3a:

In another embodiment the group R$^1$ is selected from the group R$^1$-G3a consisting of

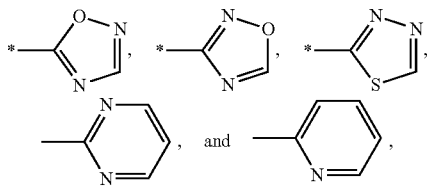

wherein each ring may be substituted with one substituent selected from the group consisting of Cl, CF$_3$, C$_{1-4}$ alkyl, —O—C$_{1-4}$ alkyl and cyclopropyl.

R$^1$-G3b:

In another embodiment the group R$^1$ is selected from the group R$^1$-G3b consisting of

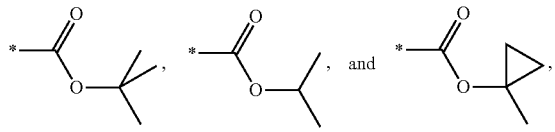

wherein each alkyl group may be substituted with 1 to 3 F atoms.

R$^1$-G3c:

In another embodiment the group R$^1$ is selected from the group R$^1$-G3c consisting of

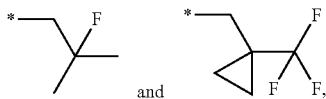

R$^1$-G4:

In another embodiment the group R$^1$ is selected from the group R$^1$-G4 consisting of

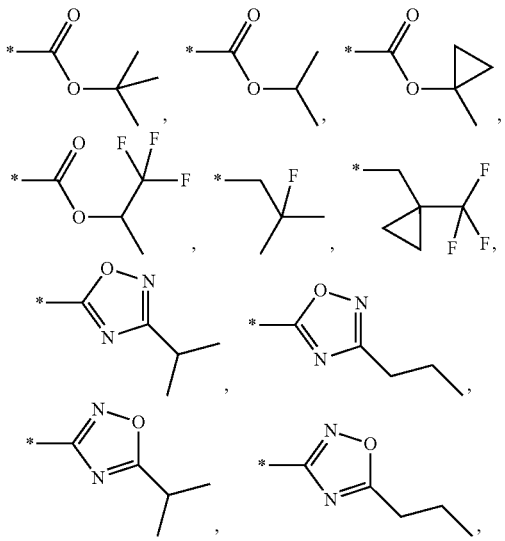

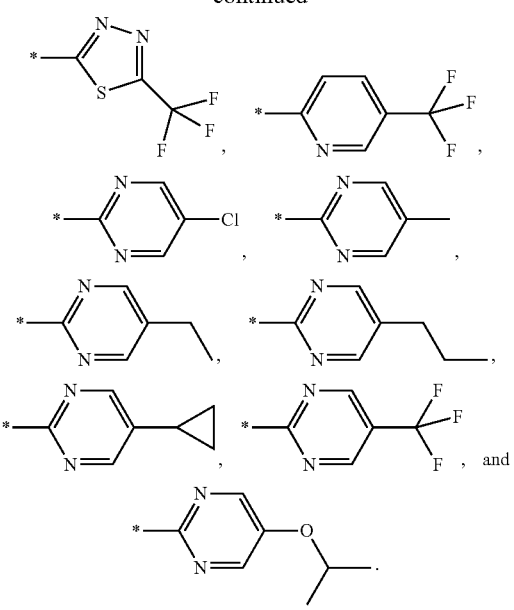

R$^1$-G4a:

In another embodiment the group R$^1$ is selected from the group R$^1$-G4a consisting of

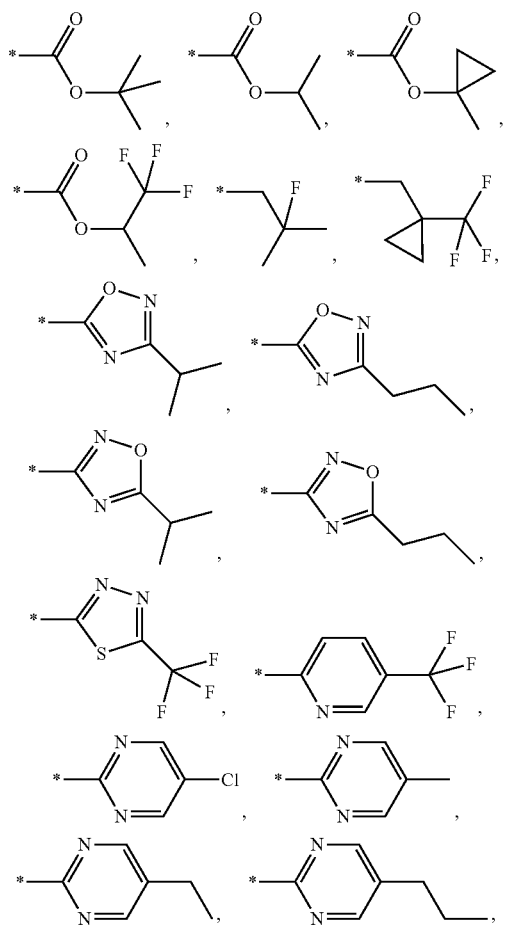

-continued

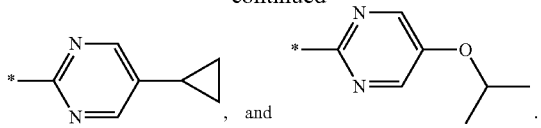

R¹-G5:

In another embodiment the group R¹ is selected from the group R¹-G5 consisting of

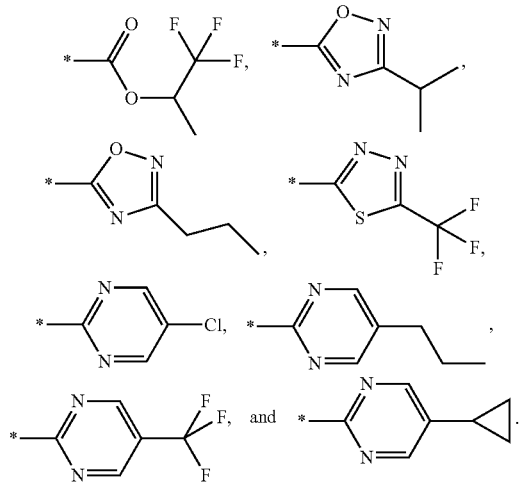

R¹-G5a:

In another embodiment the group R¹ is selected from the group R¹-G5a consisting of

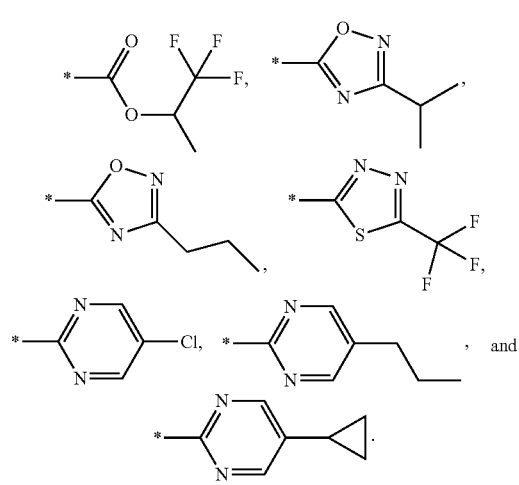

A:
A-G1:

The group A is preferably selected from the group A-G1 as defined hereinbefore and hereinafter.

A-G2:

In one embodiment the group A is selected from the group A-G2 consisting of a) phenyl, pyridyl, pyrazinyl, pyridazinyl, and pyrimidinyl, wherein each ring may be substituted with a group T and optionally substituted with one or two groups independently of each other selected from $L^A$; and b) piperidin-4-yl, 1,2,3,6-tetrahydropyridin-4-yl, 5-methyl-1,2,3,6-tetrahydropyridin-4-yl, and piperazin-1-yl, each of which is substituted at the N with a $C_{1-3}$-alkyl-S(=O)$_2$— group.

A-G3:

In another embodiment the group A is selected from the group A-G3 consisting of

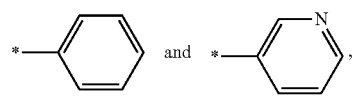

each of which is substituted with a group T and may be additionally substituted with one CN group or with one or two groups independently selected from F and $H_3C$—; and a group selected from:

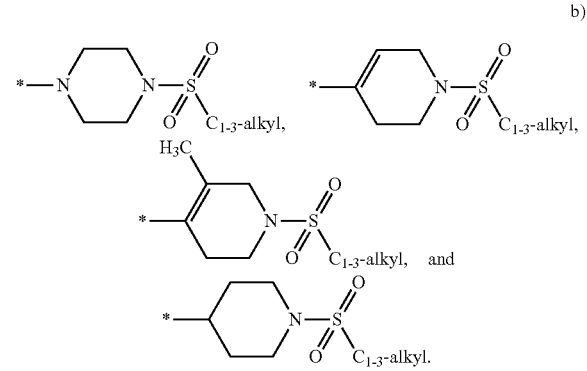

A-G3a:

In another embodiment the group A is selected from the group A-G3a consisting of

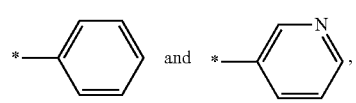

each of which is substituted with a group T and may be additionally substituted with one or two groups independently selected from F and $H_3C$—; and a group selected from:

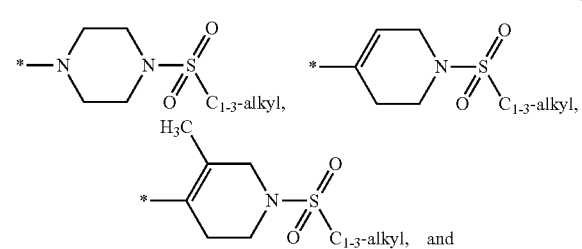

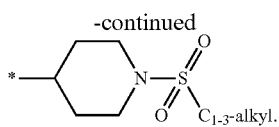

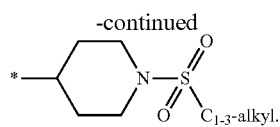

A-G4:

In another embodiment the group A is selected from the group A-G4 consisting of

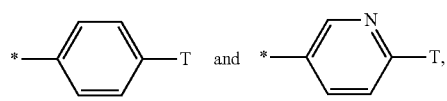  a)

each of which may be additionally substituted with one CN group or with one or two F atoms and wherein the group T is defined as hereinbefore and hereinafter; and
a group selected from:

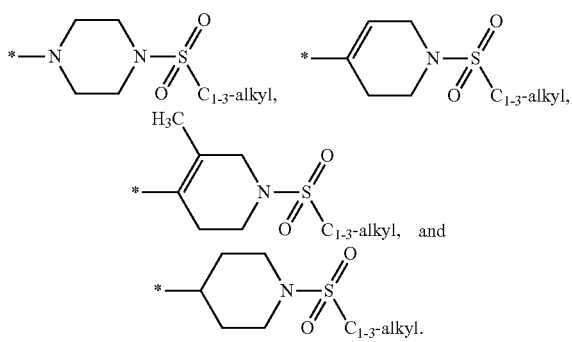  b)

A-G4p:

In another embodiment the group A is selected from the group A-G4p consisting of

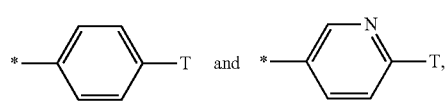  a)

each of which may be additionally substituted with one or two F atoms and wherein the group T is defined as hereinbefore and hereinafter; and
a group selected from:

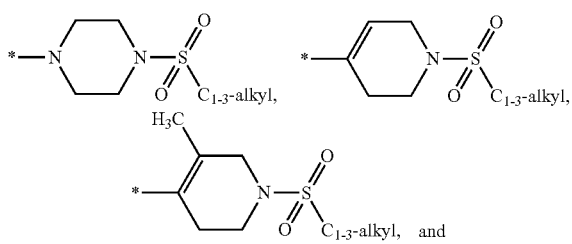  b)

A-G4a:

In another embodiment the group A is selected from the group A-G4a consisting of

which may be additionally substituted with one CN group or with one or two F atoms and wherein the group T is defined as hereinbefore and hereinafter.

A-G4aa:

In another embodiment the group A is selected from the group A-G4aa consisting of

which may be additionally substituted with one or two F atoms and wherein the group T is defined as hereinbefore and hereinafter.

A-G4b:

In another embodiment the group A is selected from the group A-G4b consisting of

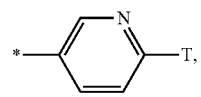

which may be additionally substituted with one or two F atoms and wherein the group T is defined as hereinbefore and hereinafter.

A-G4c:

In another embodiment the group A is selected from the group A-G4c consisting of

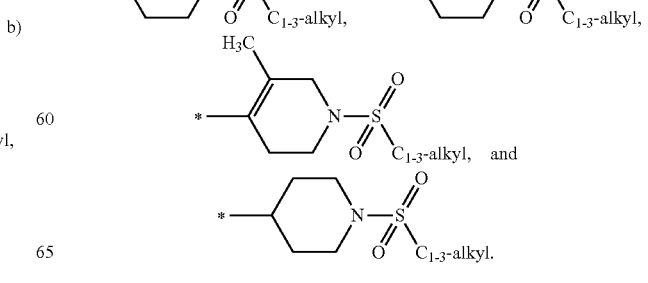

A-G4d:
In another embodiment the group A is selected from the group A-G4d consisting of

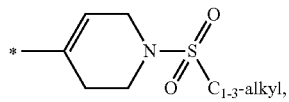

preferably

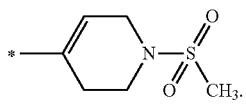

A-G5:
In another embodiment the group A is selected from the group A-G5 consisting of:

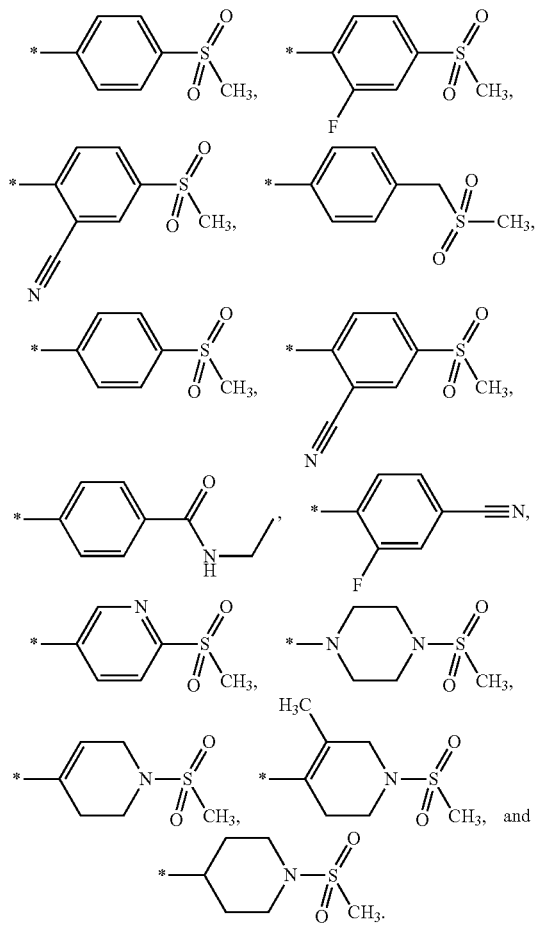

A-G5a:
In another embodiment the group A is selected from the group A-G5a consisting of:

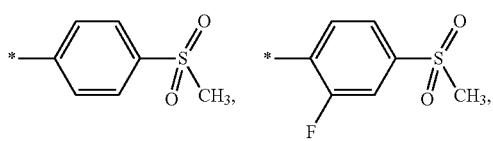

-continued

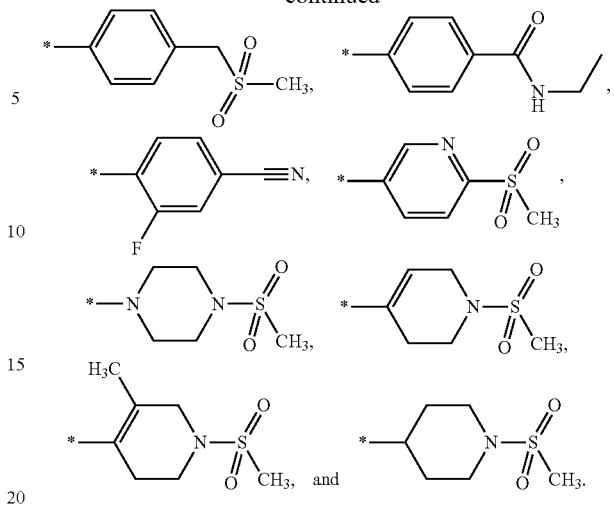

T
T-G1:
The group T is preferably selected from the group T-G1 as defined hereinbefore and hereinafter.
T-G2:
According to one embodiment the group T is selected from the group T-G2 consisting of F, Cl, Br, CN, OH, $NO_2$, $C_{1-4}$-alkyl-, $C_{1-4}$-alkyl-O—, $C_{1-4}$-alkyl-S—, $C_{1-4}$-alkyl-O—C(=O)—, $C_{1-4}$-alkyl-C(=O)—, $C_{1-4}$-alkyl-S(=O)—, $C_{1-4}$-alkyl-S(=O)$_2$—, $C_{1-4}$-alkyl-S(=O)$_2$—$C_{1-4}$-alkyl-, $R^{NT1}R^{NT2}N$—C(=O)—, $R^{NT1}R^{NT2}N$—S(=O)$_2$—, $R^{NT1}R^{NT2}N$—, $R^{NT1}R^{NT2}N$—C(=O)—$C_{1-4}$-alkyl-, wherein each alkyl group may be optionally substituted with one or more substituents independently of each other selected from F, Cl, CN, OH, phenyl, heteroaryl, and heterocyclyl,
wherein heteroaryl is selected from the group consisting of pyridinyl, pyrimidinyl, pyridazinyl, pyrazinyl, pyrazolyl, imidazolyl, [1,2,4]triazolyl and tetrazolyl; and
wherein heterocyclyl is azetidinyl, pyrrolidinyl, piperidinyl, piperazinyl or morpholinyl, in which a —$CH_2$-group may be optionally replaced by a group selected from —O(=O)— and —S(=O)$_2$—, wherein heterocyclyl group may be optionally substituted with one or more substituents independently of each other selected from $C_{1-3}$-alkyl; and
wherein phenyl and heteroaryl may be optionally substituted independently of each other with one or more substituents $L^{Pt}$.
T-G2a:
According to one embodiment the group T is selected from the group T-G2a consisting of F, Cl, Br, CN, OH, $NO_2$, $C_{1-4}$-alkyl-, $C_{1-4}$-alkyl-O—, $C_{1-4}$-alkyl-O—C(=O)—, $C_{1-4}$-alkyl-C(=O)—, $C_{1-4}$-alkyl-S(=O)—, $C_{1-4}$-alkyl-S(=O)$_2$—, $C_{1-4}$-alkyl-S(=O)$_2$—$C_{1-4}$-alkyl-, $R^{NT1}R^{NT2}N$—C(=O)—, $R^{NT1}R^{NT2}N$—S(=O)$_2$—, $R^{NT1}R^{NT2}N$—, $R^{NT1}R^{NT2}N$—C(=O)—$C_{1-4}$-alkyl-, wherein each alkyl group may be optionally substituted with one or more substituents independently of each other selected from F, Cl, CN, OH, phenyl, heteroaryl, and heterocyclyl,
wherein heteroaryl is selected from the group consisting of pyridinyl, pyrimidinyl, pyridazinyl, pyrazinyl, pyrazolyl, imidazolyl, [1,2,4]triazolyl and tetrazolyl; and
wherein heterocyclyl is azetidinyl, pyrrolidinyl, piperidinyl, piperazinyl or morpholinyl, in which a —$CH_2$-group may be optionally replaced by a group selected from —C(=O)— and —S(=O)$_2$—, wherein heterocyclyl group may be optionally substituted with one or more substituents independently of each other selected from $C_{1-3}$-alkyl; and
wherein phenyl and heteroaryl may be optionally substituted independently of each other with one or more substituents $L^A$.

T-G3:

According to another embodiment the group T is selected from the group T-G3 consisting of —CN, $C_{1-4}$-alkyl-S—, $C_{1-4}$-alkyl-S(=O)$_2$—CH$_2$—, $C_{1-4}$-alkyl-S(=O)$_2$—, $R^{NT1}R^{NT2}$N—S(=O)$_2$—, $R^{NT1}R^{NT2}$N—C(=O)—, and $R^{NT1}R^{NT2}$N—.

T-G3a:

According to another embodiment the group T is selected from the group T-G3a consisting of —CN, $C_{1-4}$-alkyl-S(=O)$_2$—CH$_2$—, $C_{1-4}$-alkyl-S(=O)$_2$—, $R^{NT1}R^{NT2}$N—S(=O)$_2$—, $R^{NT1}R^{NT2}$N—C(=O)—, and $R^{NT1}R^{NT2}$N—.

T-G4:

According to another embodiment the group T is selected from the group T-G4 consisting of NC—, $C_{1-4}$-alkyl-S—, $C_{1-4}$-alkyl-S(=O)$_2$—CH$_2$—, $C_{1-4}$-alkyl-S(=O)$_2$—, and $R^{NT1}R^{NT2}$N—C(=O)—.

T-G4a:

According to another embodiment the group T is selected from the group T-G4a consisting of NC—, $C_{1-4}$-alkyl-S(=O)$_2$—CH$_2$—, $C_{1-4}$-alkyl-S(=O)$_2$—, and $R^{NT1}R^{NT2}$N—C(=O)—.

T-G5:

According to another embodiment the group T is selected from the group T-G5 consisting of NC—, CH$_3$—S—, CH$_3$—CH$_2$—NH—C(=O)—, CH$_3$—S(=O)$_2$—CH$_2$—, and CH$_3$—S(=O)$_2$—.

T-G5a:

According to another embodiment the group T is selected from the group T-G5a consisting of NC—, CH$_3$—CH$_2$—NH—C(=O)—, CH$_3$—S(=O)$_2$—CH$_2$—, and CH$_3$—S(=O)$_2$—.

$R^N$ $R^N$-G1:

The group $R^N$ is preferably selected from the group $R^N$-G1 as defined hereinbefore and hereinafter.

$R^N$-G2:

In another embodiment the group $R^N$ is selected from the group $R^N$-G2 consisting of H, methyl, ethyl, isopropyl, methylcarbonyl, and methylsulfonyl.

$R^N$-G3:

In another embodiment the group $R^N$ is selected from the group $R^N$-G3 consisting of H, methyl, methylcarbonyl, and methylsulfonyl.

$R^N$-G4:

In another embodiment the group $R^N$ is selected from the group $R^N$-G4 consisting of H and methyl.

$R^{NT1}$ $R^{NT1}$-G1:

$R^{NT1}$ is preferably selected from the group $R^{NT1}$-G1 as defined hereinbefore and hereinafter.

$R^{NT1}$-G2:

In another embodiment $R^{NT1}$ is selected from the group $R^{NT1}$-G2 consisting of H, $C_{1-4}$-alkyl, $C_{3-6}$-cycloalkyl, tetrahydropyranyl, wherein each alkyl and cycloalkyl group may be optionally substituted with one substituent selected from the group consisting of F, CH$_3$, OH, $C_{1-3}$-alkyl-O—, $(R^N)_2$N, CN, tetrahydrofuranyl, 1,4-dioxinyl, oxazolyl, and pyridyl.

$R^{NT1}$-G3:

In another embodiment $R^{NT1}$ is selected from the group $R^{NT1}$-G3 consisting of H, $C_{1-4}$-alkyl and $C_{3-6}$-cycloalkyl, wherein each alkyl and cycloalkyl group may be optionally substituted with one substituent selected from F, CH$_3$, OH, and $C_{1-3}$-alkyl-O—.

$R^{NT1}$-G4:

In another embodiment $R^{NT1}$ is selected from the group $R^{NT1}$-G4 consisting of H and $C_{1-4}$-alkyl.

$R^{NT2}$ $R^{NT2}$-G1:

$R^{NT2}$ is preferably selected from the group $R^{NT2}$-G1 as defined hereinbefore and hereinafter.

$R^{NT2}$-G2:

In another embodiment $R^{NT2}$ is selected from the group $R^{NT2}$-G2 consisting of H and $C_{1-3}$-alkyl.

$R^{NT2}$-G3:

In another embodiment $R^{NT2}$ is selected from the group $R^{NT2}$-G3 consisting of H and methyl.

$R^{NT2}$-G4:

In another embodiment $R^{NT2}$ is selected from the group $R^{NT2}$-G4 consisting of H.

$R^{NT1}R^{NT2}$ $R^{NT1}R^{NT2}$-G1:

According to one embodiment the groups $R^{NT1}$ and $R^{NT2}$ are linked and form a group which is selected from the group $R^{NT1}R^{NT2}$-G1 as defined hereinbefore and hereinafter.

$R^{NT1}R^{NT2}$-G2:

According to another embodiment the groups $R^{NT1}$ and $R^{NT2}$ are linked and together with the N-atom to which they are attached form a group which is selected from the group $R^{NT1}R^{NT2}$-G2 consisting of azetidinyl, pyrrolidinyl, piperidinyl, morpholinyl, piperazinyl, piperazin-2-onyl, N—$C_{1-3}$-alkyl-piperazinyl, N—$C_{1-3}$-alkyl-piperazin-2-onyl, and N—($C_{1-3}$-alkyl-C(=O))-piperazinyl, which may be optionally substituted with one or more substituents independently of each other selected from the group consisting of F, HO, $C_{1-3}$-alkyl, $C_{1-3}$-alkyl-O—, and $(R^N)_2$N.

$R^{NT1}R^{NT2}$-G3:

According to another embodiment the groups $R^{NT1}$ and $R^{NT2}$ are linked and together with the N-atom to which they are attached form a group which is selected from the group $R^{NT1}R^{NT2}$-G3 consisting of azetidinyl, pyrrolidinyl, piperidinyl, and morpholinyl, each of which may be optionally substituted with one or two substituents independently of each other selected from the group consisting of F, OH, CH$_3$ and CH$_3$—O—.

$L^A$:

$L^A$-G1:

The group $L^A$ is preferably selected from the group $L^A$-G1 as defined hereinbefore and hereinafter.

$L^A$-G2:

In another embodiment the group $L^A$ is selected from the group $L^A$-G2 consisting of F, Cl, Br, CN, OH, $C_{1-3}$-alkyl-, $C_{1-3}$-alkyl-O—, H$_2$N—, $C_{1-3}$-alkyl-NH— and ($C_{1-3}$-alkyl)$_2$N—, wherein the $C_{1-3}$-alkyl- and $C_{1-3}$-alkyl-O— group may be optionally substituted with one or more F-atoms.

$L^A$-G3:

In another embodiment the group $L^A$ is selected from the group $L^A$-G3 consisting of F, Cl, CN, CH$_3$, and CF$_3$.

$L^A$-G3a:

In another embodiment the group $L^A$ is selected from the group $L^A$-G3a consisting of F, Cl, CH$_3$, and CF$_3$.

$R^C$:

$R^C$-G1:

The group $R^C$ is preferably selected from the group $R^C$-G1 as defined hereinbefore and hereinafter.

$R^C$-G2:

According to one embodiment the group $R^C$ is selected from the group $R^C$-G2 consisting of F, Cl, Br, I, CN, OH, $C_{1-6}$-alkyl-, $C_{2-6}$-alkenyl-, $C_{2-6}$-alkynyl-, $C_{3-6}$-cycloalkyl, $C_{1-6}$-alkyl-O—, $C_{3-6}$-cycloalkyl-O—, $C_{1-6}$-alkyl-S—, $C_{1-6}$-alkyl-O—C(=O)—, $C_{1-4}$-alkyl-S(=O)—, $C_{1-4}$-alkyl-S(=O)—$C_{1-4}$-alkyl-, $C_{1-4}$-alkyl-S(=O)$_2$—, $C_{1-4}$-alkyl-S(=O)$_2$—$C_{1-4}$-alkyl-, $R^{NT1}R^{NT2}N$—, $R^{NT1}R^{NT2}N$—$C_{1-3}$-alkyl-, $R^{NT1}R^{NT2}N$—C(=O)—, $R^{NT1}R^{NT2}N$—S(=O)$_2$—, $R^{NT1}R^{NT2}N$—S(=O)$_2$—$C_{1-4}$-alkyl-, $R^{NT1}R^{NT2}N$—C(=O)—$C_{1-4}$-alkyl-, heterocyclyl, heterocyclyl-O—, and phenyl, wherein each alkyl, alkenyl, alkynyl, and cycloalkyl group may be optionally substituted with one or more fluorine atoms and a substituent selected from Cl, CN, OH, $C_{1-3}$-alkyl, $C_{3-6}$-cycloalkyl, $C_{1-3}$-alkyl-O—, and heterocyclyl;

wherein heterocyclyl is selected from the group consisting of pyrrolidin-2-onyl, piperidin-2-onyl, piperazin-2-onyl, morpholinyl, morpholin-3-onyl, oxetanyl, tetrahydrofuranyl, and tetrahydropyranyl, each of which may be optionally substituted with one or two $H_3C$— groups; and wherein phenyl may be optionally substituted independently of each other with one or more substituents $L^{P_t}$.

$R^C$-G3:

According to another embodiment the group $R^C$ is selected from the group $R^C$-G3 consisting of F, Cl, Br, CN, $C_{1-4}$-alkyl-, $C_{3-6}$-cycloalkyl, $C_{1-4}$-alkyl-O—, $C_{3-6}$-cycloalkyl-O—, heterocyclyl, and heterocyclyl-O—, wherein each alkyl and cycloalkyl group may be optionally substituted with one or more fluorine atoms and a substituent selected from $H_3C$— and $H_3C$—O—, and wherein heterocyclyl is selected from the group consisting of oxetanyl, tetrahydrofuranyl, and tetrahydropyranyl, each of which may be optionally substituted with one or two $H_3C$— groups.

$R^C$-G4:

According to another embodiment the group $R^C$ is selected from the group $R^C$-G4 consisting of F, Cl, $C_{1-4}$-alkyl, $F_3C$—, $C_{3-4}$-cycloalkyl, and $C_{1-3}$-alkyl-O—.

$R^C$-G5:

According to another embodiment the group $R^C$ is selected from the group $R^C$-G5 consisting of Cl, $C_{1-3}$-alkyl, cyclopropyl, $F_3C$—, and isopropyl-O—.

Examples of preferred subgeneric embodiments according to the present invention are set forth in the following table, wherein each substituent group of each embodiment is defined according to the definitions set forth hereinbefore and wherein all other substituents of the formula I are defined according to the definitions set forth hereinbefore:

| Embodiment | $R^1$- | A- | T- | $R^C$- | $L^A$ |
|---|---|---|---|---|---|
| E-1 | $R^1$-G1 | A-G1 | T-G1 | $R^C$-G1 | $L^A$-G2 |
| E-2 | $R^1$-G2 | A-G2 | T-G3 | $R^C$-G3 | $L^A$-G3 |
| E-3 | $R^1$-G2 | A-G2 | T-G3 | $R^C$-G3 | F |
| E-4 | $R^1$-G3 | A-G3 | T-G4 | $R^C$-G4 | — |
| E-5 | $R^1$-G3 | A-G3 | T-G5 | $R^C$-G5 | — |
| E-6 | $R^1$-G4 | A-G4 | T-G4 | — | — |
| E-7 | $R^1$-G4 | A-G4 | T-G5 | — | — |
| E-8 | $R^1$-G4 | A-G5 | — | — | — |
| E-9 | $R^1$-G5 | A-G4d | — | — | — |
| E-10 | $R^1$-G5 | preferred rest of A-G4d | — | — | — |

Preferred are those compounds of formula I, wherein $R^1$ is selected from the group consisting of

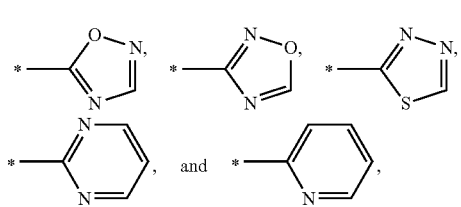

a)

wherein each ring may be optionally substituted with one substituent $R^C$; and a group selected from:

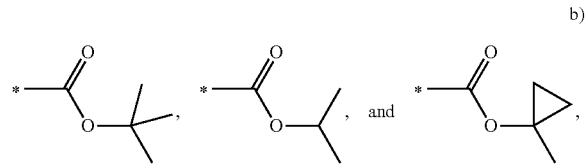

b)

wherein each alkyl residue may be substituted with 1 to 3 F atoms; and a group selected from:

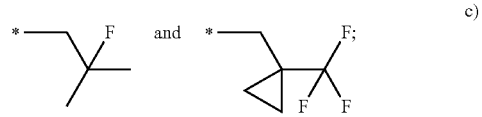

c)

$R^C$ is selected from the group consisting of Cl, $C_{1-3}$-alkyl, cyclopropyl, $F_3C$—, and isopropyl-O—;

A is selected from the group consisting of

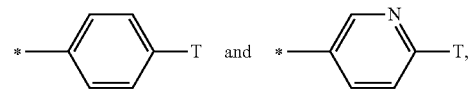

a)

each of which may be additionally substituted with one CN group or with one or two F atoms and wherein the group T is selected from the group consisting of NC—, $CH_3$—$CH_2$—NH—C(=O)—, $CH_3$—S(=O)$_2$—$CH_2$—, and $CH_3$—S(=O)$_2$—; and b)

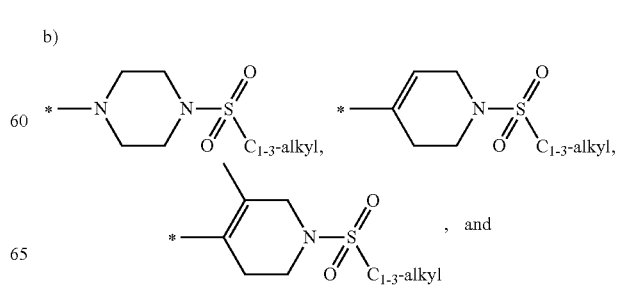

-continued

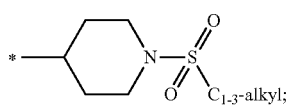

and the pharmaceutically acceptable salts thereof.

More preferred are those compounds of formula I, wherein $R^1$ is selected from the group consisting of:

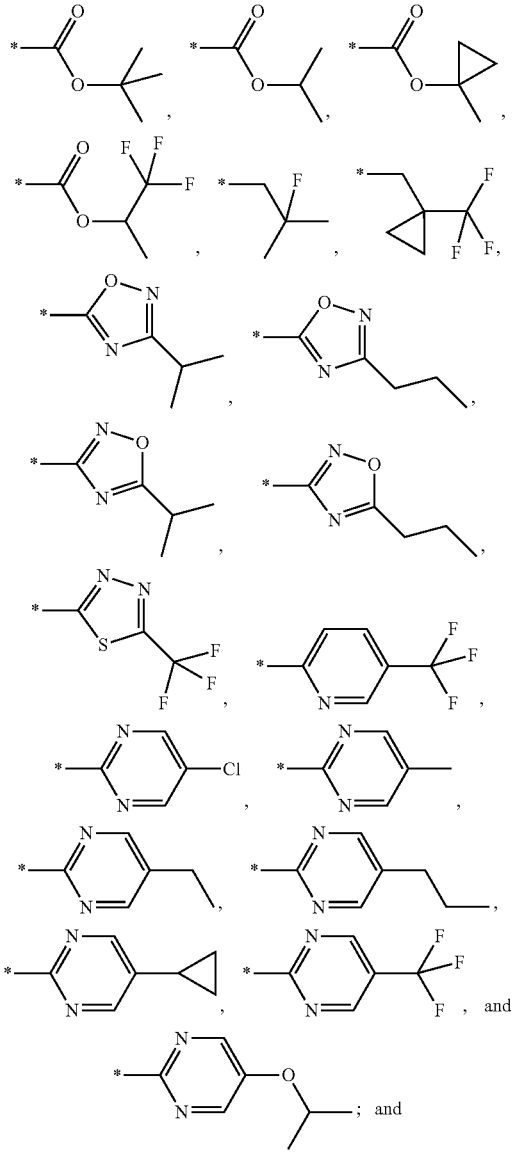

; and

A is selected from the group consisting of

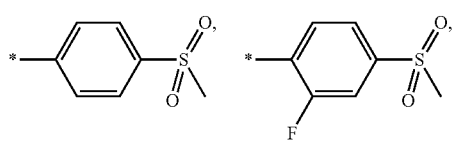

-continued

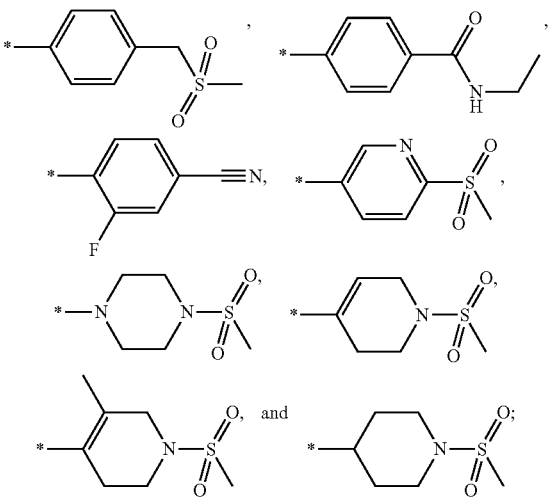

and the pharmaceutically acceptable salts thereof.

Even more preferred are those compounds of formula I, wherein
$R^1$ is selected from the group consisting of:

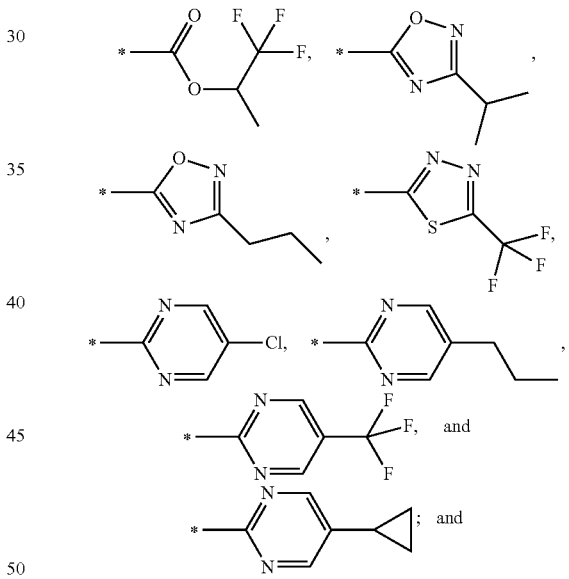

A is selected from the group consisting of

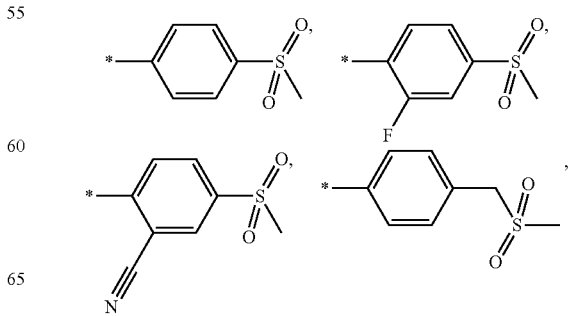

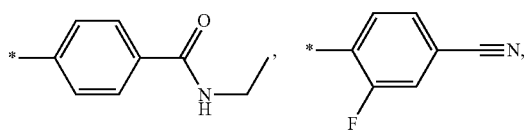

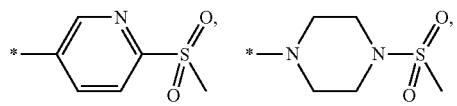

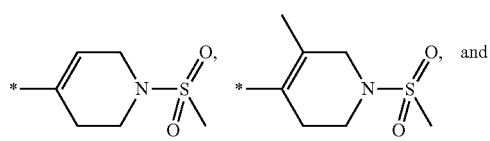

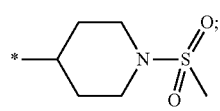

and the pharmaceutically acceptable salts thereof.

Most preferred are those compounds of formula I, wherein R¹ is selected from the group consisting of:

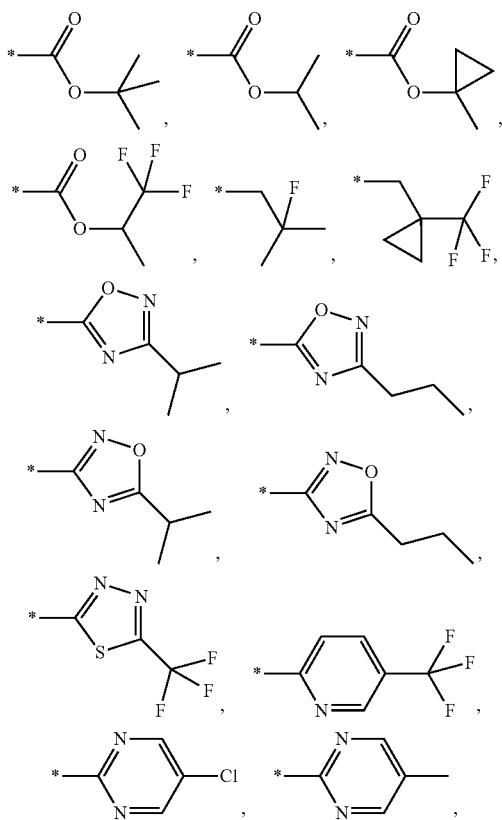

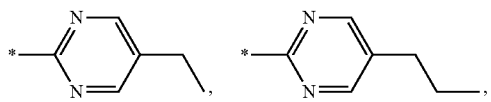

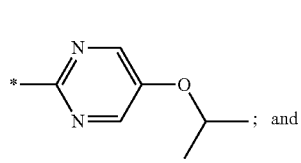

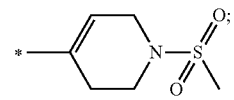

A is

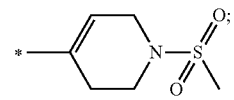

and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to persons skilled in the art but are not described in detail here may also be used. The general processes for preparing the compounds according to the invention will become apparent to a person skilled in the art on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to one skilled in the art.

Compounds of the invention I are preferably accessed from the intermediates 1 and 2 that are combined with 3 and 4, respectively (Scheme 1); R¹ and A have the meanings as defined hereinbefore and hereinafter.

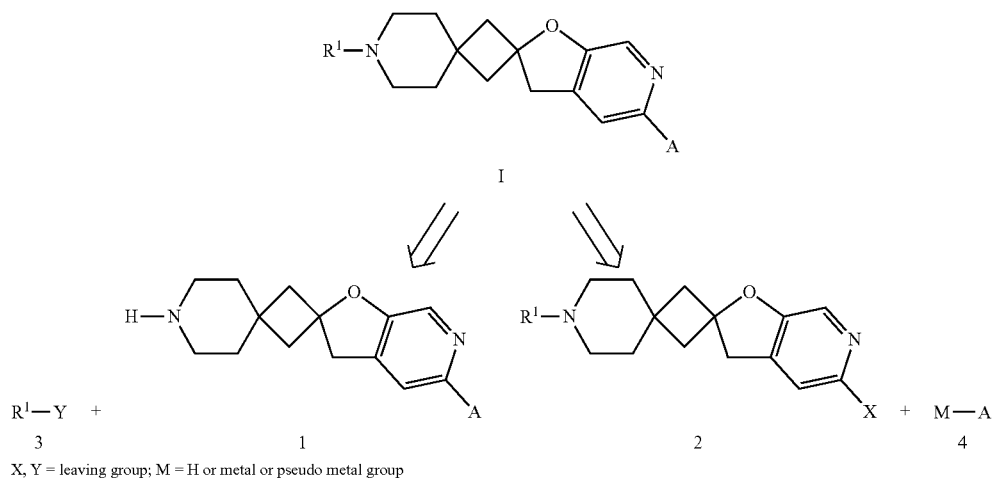

Intermediates 1 and 2 may be obtained from ketone 5 and pyridine 6 as delineated in Scheme 2; $R^1$ and A have the meanings as defined hereinbefore and hereinafter. Accordingly, pyridine 6, bearing two potential leaving groups, is treated with a strong base, such as lithium hexamethyldisilazide and lithium diisopropylamide, to form the anion at the methyl carbon atom which is subsequently added to ketone 5 to give alcohol 7. The reaction is preferably conducted in inert solvents, such as hexanes, toluene, ether, tetrahydrofuran, 1,2-dimethoxyethane, and mixtures thereof, at low temperature, between −80 and 0° C.

Dispiro compound 8 is obtained by cyclization from compound 7. Cyclization is preferably accomplished by a transition metal mediated reaction from a compound 7 bearing a leaving group $X^2$ on the pyridine; $X^2$ is preferably Cl, Br, or I. Palladium in combination with a ligand, e.g. palladium acetate combined with 2-(di-tert-butylphosphino)-1,1'-binaphthyl, may give a suited transition metal complex for this purpose. The reaction is preferably conducted in the presence of a base, e.g. $K_2CO_3$ and $Cs_2CO_3$, in a solvent, e.g. toluene, 1,4-dioxane, N,N-dimethylformamide, N,N-dimethylacetamide, N-methylpyrrolidone, or mixtures thereof, at elevated temperature, preferably at 40 to 180° C.

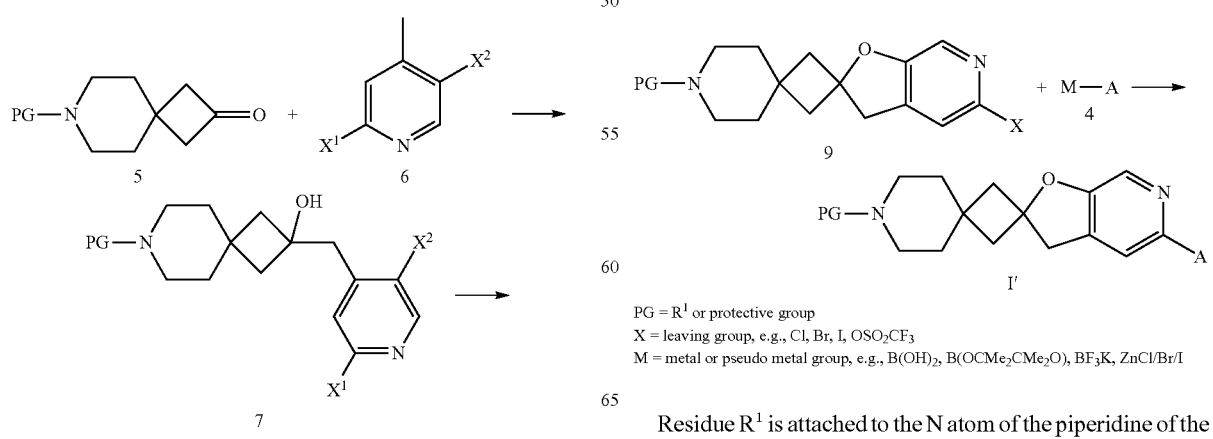

$PG = R^1$ or protective group, e.g., $PhCH_2OC(=O)$
$X^1 = A$ or halogen or pseudo-halogen group, e.g., Cl, Br, I, $OSO_2CF_3$
$X^2 =$ halogen or pseudo-halogen group, e.g., Cl, Br, I, $OSO_2CF_3$ Residue A is attached to compound 9 preferably via a transition metal catalyzed coupling reaction (Scheme 3); A and $R^1$ are defined as hereinbefore and hereinafter. A is preferably used as the nucleophilic, e.g. as boronic acid or ester, and compound 9 as the electrophilic component, e.g. as chloride or bromide. A palladium complex is the preferred catalyst which is formed in situ from a suited palladium precursor and ligands, e.g. $Pd(PPh_3)_4$ or $PdCl_2[1,1'$-bis(diphenylphosphino)ferrocene]. The reaction using A as boronic acid or ester is usually conducted in the presence of a base, e.g. $Na_2CO_3$ or $K_2CO_3$, preferably in an aqueous or alcoholic solvent, e.g. water and 1,4-dioxane or toluene, at elevated temperature, preferably between 60 and 160° C.

$PG = R^1$ or protective group
$X =$ leaving group, e.g., Cl, Br, I, $OSO_2CF_3$
$M =$ metal or pseudo metal group, e.g., $B(OH)_2$, $B(OCMe_2CMe_2O)$, $BF_3K$, ZnCl/Br/I Residue $R^1$ is attached to the N atom of the piperidine of the compounds of the invention via different routes depending on the nature of residue $R^1$ (Scheme 4); $R^1$ and A have the meanings as defined hereinbefore and hereinafter.

A heteroaryl group may be attached via a nucleophilic substitution of a leaving group on the heteroaromatic, such as F, Cl, Br, $SO_2C_{1-4}$-alkyl, or $SO_2$aryl. The reaction is preferably conducted in the presence of a base, e.g. $Na_2CO_3$, $K_2CO_3$, $Cs_2CO_3$, triethylamine, ethyldiisopropylamine, or 1,8-diazabicyclo[5.4.0]undec-7-ene, in toluene, tetrahydrofuran, 1,4-dioxane, 1,2-dimethoxyethane, acetonitrile, N,N-dimethylformamide, N,N-dimethylacetamide, N-methylpyrrolidinone, water, alcohol, dimethyl sulfoxide, or mixtures thereof, at 20 to 220° C. by conventional or microwave heating. In certain cases the use of transition metal catalysts may be beneficial or even essential. The leaving group Y in compound 3 is then preferably Cl, Br, I, and $OSO_2CF_3$. Some heteroaromatic residues $R^1$ such as [1,2,4]oxadiazoles may also be assembled from the corresponding cyanamide of compound 10 and N-hydroxyamidine.

A carbamate group may be formed from compound 10 and an oxycarbonyl electrophile ($R^1=R^aO-C(=O)$), such as $R^aO-C(=O)-Cl$ or $R^aO-C(=O)-O-C(=O)-OR^a$. The reaction is usually conducted in the presence of a base, e.g. $K_2CO_3$, pyridine, 4-dimethylaminopyridine, triethylamine, or ethyldiisopropylamine, in a solvent such as toluene, dichloromethane, ether, tetrahydrofuran, 1,4-dioxane, 1,2-dimethoxyethane, acetonitrile, or mixtures thereof, at −10 to 120° C.

A methylene group may be attached to the piperidine N by using an $R^1$ group bearing a leaving group at the $CH_2$ unit to be attached, such as Cl, Br, I, $OSO_2C_{1-4}$-alkyl, $OSO_2$aryl, or $OSO_2CF_3$. The substitution is commonly done in the presence of a base, e.g. $Na_2CO_3$, $K_2CO_3$, $Cs_2CO_3$, pyridine, triethylamine, ethyldiisopropylamine, or 1,8-diazabicyclo[5.4.0]undec-7-ene, in a solvent such as toluene, tetrahydrofuran, 1,4-dioxane, 1,2-dimethoxyethane, acetonitrile, N,N-dimethylformamide, N,N-dimethylacetamide, N-methylpyrrolidinone, water, methanol, ethanol, isopropanol, dimethyl sulfoxide, or mixtures thereof, at 20 to 220° C. by conventional or microwave heating.

Alternatively, the $CH_2$ moiety of residue $R^1$ is formed during the attachment reaction by reductive alkylation employing $R^1$ as aldehyde and a reducing agent, such as $NaH_3BCN$ or $NaHB(O_2CCH_3)_3$. Using a carboxylic acid derivative of $R^1$ also allows the attachment of $R^1$ to intermediate 10 via a $CH_2$ unit by a two step procedure, amide coupling followed by reduction of the amide carbonyl group.

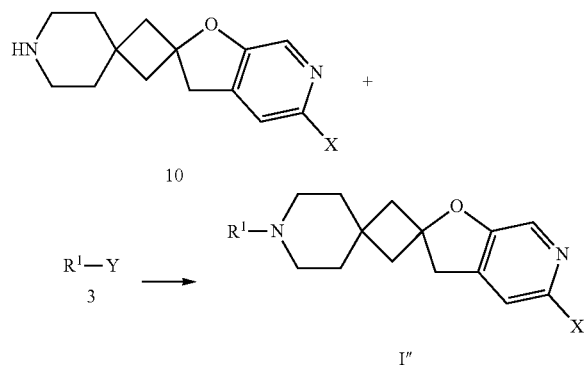

Scheme 4

Y = leaving group, e.g., Cl
X = A or leaving group, e.g., Cl, Br, I

The synthetic routes presented may rely on the use of protecting groups. For example, potentially reactive groups present, such as hydroxy, carbonyl, carboxy, amino, alkylamino, or imino, may be protected during the reaction by conventional protecting groups which are cleaved again after the reaction. Suitable protecting groups for the respective functionalities and their removal are well known to the one skilled in the art and are described in the literature of organic synthesis.

The compounds of general formula I may be resolved into their enantiomers and/or diastereomers as mentioned before. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of general formula I which occur as racemates may be separated by methods known per se into their optical antipodes and diastereomeric mixtures of compounds of general formula I may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned above.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula I may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the persons skilled in the art from the literature.

TERMS AND DEFINITIONS

Terms not specifically defined herein should be given the meanings that would be given to them by one skilled in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the activation of the G-protein-coupled receptor GPR119 with one or more compounds of the present invention.

The terms "mediated" or "mediating" or "mediate", as used herein, unless otherwise indicated, refers to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

The numeration of the atoms of a substituent starts with the atom which is closest to the core or to the group to which the substituent is attached.

For example, the term "3-carboxypropyl-group" represents the following substituent:

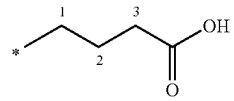

wherein the carboxy group is attached to the third carbon atom of the propyl group. The terms "1-methylpropyl-", "2,2-dimethylpropyl-" or "cyclopropylmethyl-" group represent the following groups:

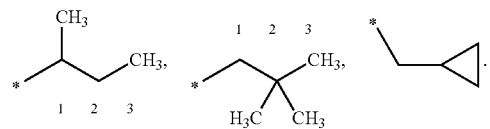

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof.

Acid salts which are for example useful for purifying or isolating the compounds of the present invention are also part of the invention.

The term halogen generally denotes fluorine, chlorine, bromine and iodine.

The term "$C_{1-n}$-alkyl", wherein n is an integer>1, either alone or in combination with another radical denotes an acyclic, saturated, branched or linear hydrocarbon radical with 1 to n C atoms. For example the term $C_{1-5}$-alkyl embraces the radicals H₃C—, H₃C—CH₂—, H₃C—CH₂—CH₂—, H₃C—CH(CH₃)—, H₃C—CH₂—CH₂—CH₂—, H₃C—CH₂—CH(CH₃)—, H₃C—CH(CH₃)—CH₂—, H₃C—C(CH₃)₂—, H₃C—CH₂—CH₂—CH₂—CH₂—, H₃C—CH₂—CH₂—CH(CH₃)—, H₃C—CH₂—CH(CH₃)—CH₂—, H₃C—CH(CH₃)—CH₂—CH₂—, H₃C—CH₂—C(CH₃)₂—, H₃C—C(CH₃)₂—CH₂—, H₃C—CH(CH₃)—CH(CH₃)— and H₃C—CH₂—CH(CH₂CH₃)—.

The term "$C_{1-n}$-alkylene" wherein n is an integer>1, either alone or in combination with another radical, denotes an acyclic, straight or branched chain divalent alkyl radical containing from 1 to n carbon atoms. For example the term $C_{1-4}$-alkylene includes —(CH₂)—, —(CH₂—CH₂)—, —(CH(CH₃))—, —(CH₂—CH₂—CH₂)—, —(C(CH₃)₂)—, —(CH(CH₂CH₃))—, —(CH(CH₃)—CH₂)—, —(CH₂—CH(CH₃))—, —(CH₂—CH₂—CH₂—CH₂)—, —(CH₂—CH₂—CH(CH₃))—, —(CH(CH₃)—CH₂—CH₂)—, —(CH₂—CH(CH₃)—CH₂)—, —(CH₂—C(CH₃)₂)—, —(C(CH₃)₂—CH₂)—, —(CH(CH₃)—CH(CH₃))—, —(CH₂—CH(CH₂CH₃))—, —(CH(CH₂CH₃)—CH₂)—, —(CH(CH₂CH₂CH₃))—, —(CHCH(CH₃)₂)— and —C(CH₃)(CH₂CH₃)—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —CH=CH₂, —CH=CH—CH₃, —CH₂—CH=CH₂.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes —CH=CH—, —CH=CH—CH₂—, —CH₂—CH=CH—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —C≡CH, —C≡C—CH₃, —CH₂—C≡CH.

The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes —C≡C—, —C≡C—CH₂—, —CH₂—C≡C—.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cycloalkyl, $C_{3-10}$-cycloalkenyl, octahydropentalenyl, octahydroindenyl, decahydronaphthyl, indanyl, tetrahydronaphthyl. Most preferably the term $C_{3-n}$-carbocyclyl denotes $C_{3-n}$-cycloalkyl, in particular $C_{3-7}$-cycloalkyl.

The term "$C_{3-n}$-cycloalkyl", wherein n is an integer>3, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "$C_{3-n}$-cycloalkenyl", wherein n is an integer>3, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or S(O)ᵣ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or S(O)ᵣ with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

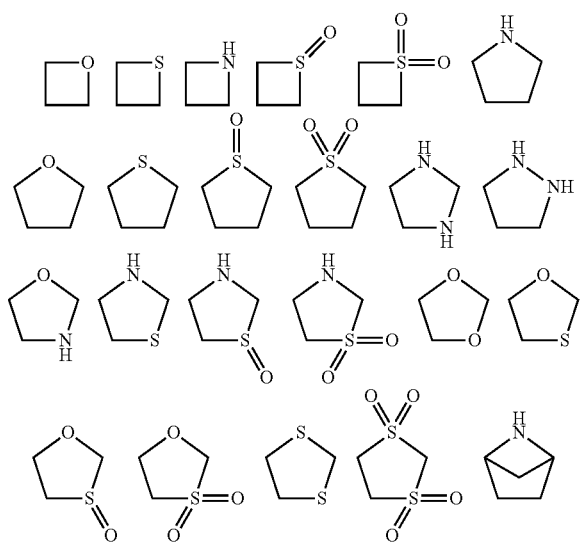

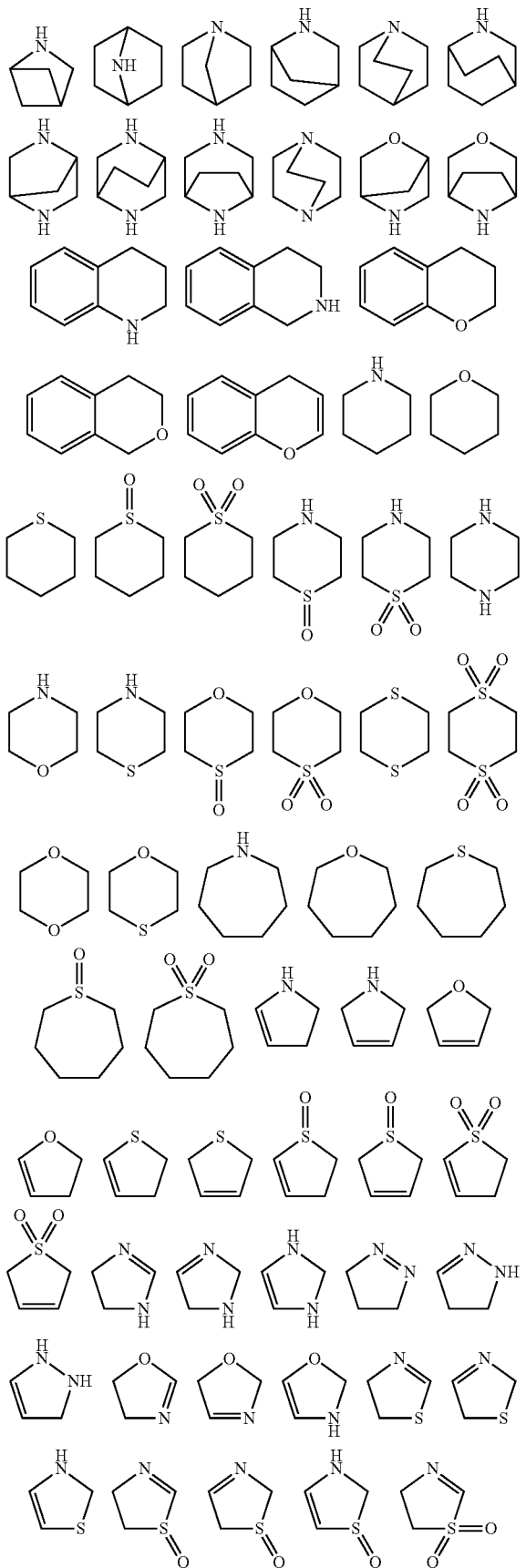
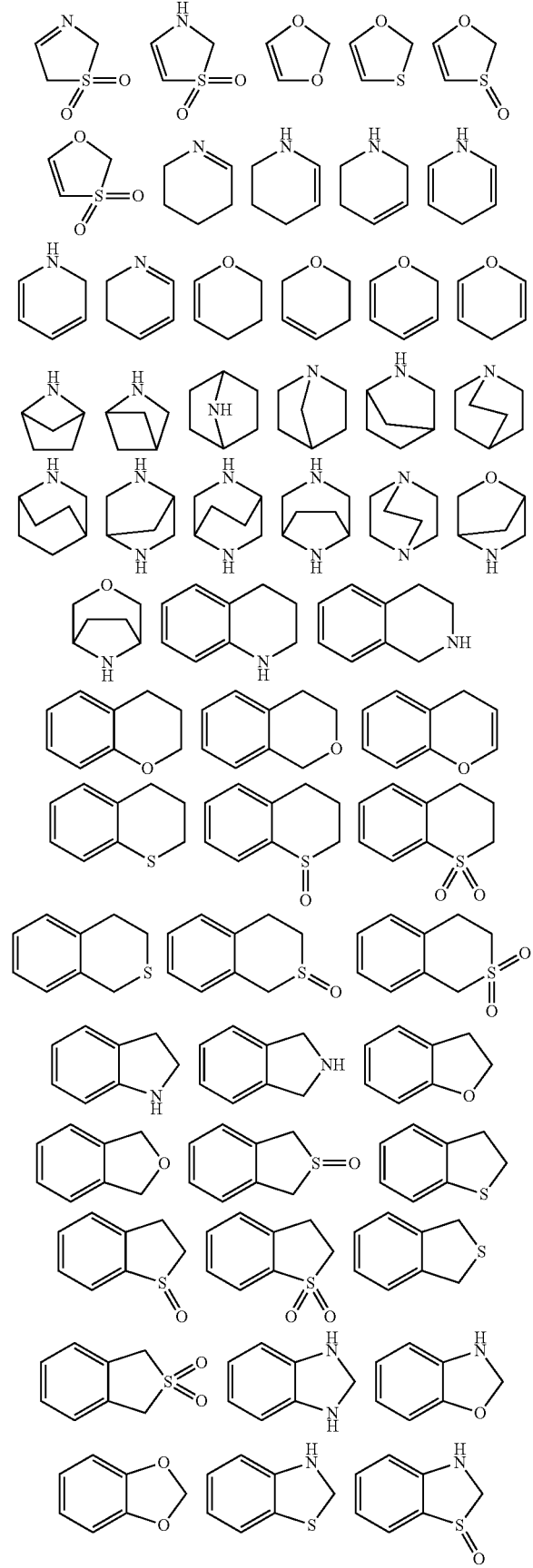

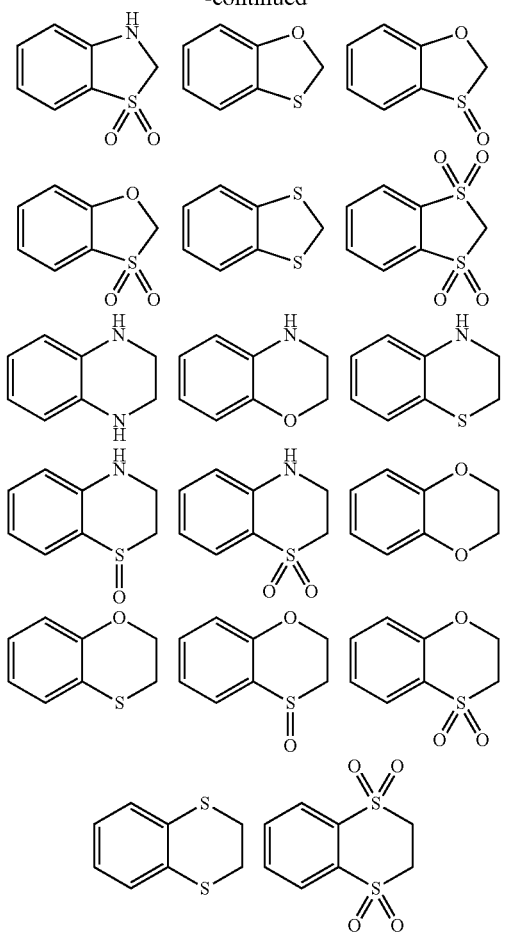

The term "heteroaryl" means a mono- or polycyclic, preferably mono- or bicyclic-ring system containing one or more heteroatoms selected from N, O or S(O)$_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic-ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

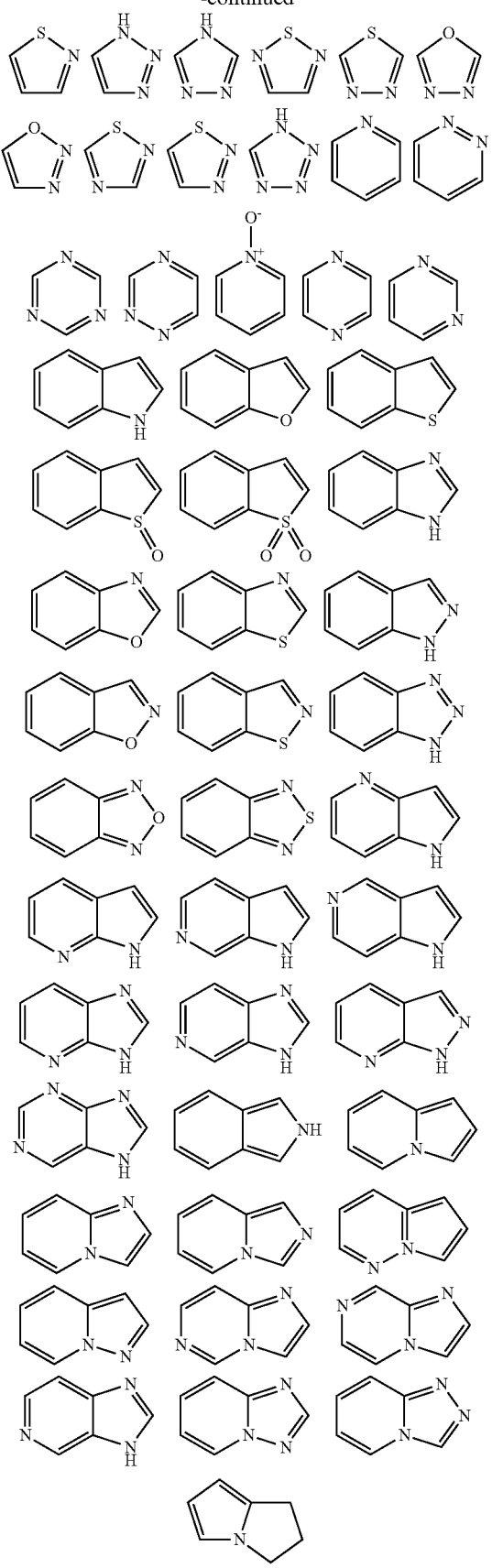

Many of the terms given above may be used repeatedly in the definition of a formula or group and in each case have one of the meanings given above, independently of one another.

Pharmacological Activity

The activity of the compounds of the invention may be demonstrated using the following assay:

The compounds of formula I according to the invention modulate the activity of the G-protein-coupled receptor GPR119. The effect of the compounds on the activation of GPR119 and on the stimulation of intracellular cAMP concentration is determined using the AlphaScreen cAMP Assay Kit (Cat. No. #6760625R) made by PerkinElmer.

MIN6 cells [Miyazaki J et al., Endocrinology. 1990 July; 127(1):126-32] are stably transfected with an expression vector for human GPR119 cDNA (Acc. No. NP_848566). Min-6/hGPR119 cells are cultured in DMEM, 10% FBS, 50 μM β-mercaptoethanol, 0.3 mg/mL Geniticin, 2 mM GlutaMAX at 37° C., 5% $CO_2$. For the assay, the cells are seeded in Optiplates (white, 384-well, 160W-barcoded, TC, sterile with lid, Cat. No. #6007688 (Perkin Elmer); 10000 cells/well; 50 μL). The plates covered with lids are then incubated for 24 hours at 37° C., 5% $CO_2$. After the medium is aspirated from the wells completely, 10 ill of the test compound are added, the compounds are diluted using stimulating buffer (140 mM NaCl, 3.6 mM KCl, 0.5 mM $NaH_2PO_4$, 0.5 mM $MgSO_4$, 1.5 mM $CaCl_2$, 10 mM Hepes, 5 mM $NaHCO_3$; pH 7.4. 0.5 mM IBMX and 0.1% BSA, the final DMSO concentration is 1%). After 45 minutes incubation at room temperature (approx. 20° C.), the cAMP concentrations are determined using the AlphaScreen cAMP Assay Kit (Cat. No. #6760625R from PerkinElmer). 10 ill of Biotin-cAMP (final concentration 1 U/well in lysing buffer (5 mM Hepes (pH 7.4), 0.1% BSA, 0.5% Tween) and 10 μL Bead solution (final concentration 1 U/well in lysing buffer) are added. The plates are incubated for another 2 hours at room temperature. The cAMP concentrations are calculated using a cAMP standard curve from the Alpha Screen Counts. The data analysis is carried out by calculating the $EC_{50}$ value and the maximum value based on a positive control, using suitable software (Graphpad Prism). The compounds according to the invention increase the intracellular cAMP level in the range of 3-5.

The compounds according to the invention typically have $EC_{50}$ values in the range from about 1 nM to about 10 μM, preferably less than 1 μM, more preferably less than 100 nM.

$EC_{50}$ values for compounds according to the invention are shown in the following Table. The number of the compound corresponds to the number of the Example in the experimental section.

| Example | $EC_{50}$ [nM] | Example | $EC_{50}$ [nM] | Example | $EC_{50}$ [nM] | Example | $EC_{50}$ [nM] |
|---|---|---|---|---|---|---|---|
| 1 | 21 | 2 | 50 | 3 | 15 | 4 | 18 |
| 5 | 362 | 6 | 135 | 7 | 42 | 8 | 19 |
| 9 | 6 | 10 | 16 | 11 | 13 | 12 | 11 |
| 13 | 42 | 14 | 60 | 15 | 10 | 16 | 4 |
| 17 | 9 | 18 | 24 | 19 | 106 | 20 | 10 |
| 21 | 77 | 22 | 28 | 23 | 12 | 24 | 10 |
| 25 | 5 | 26 | 8 | 27 | 4 | 28 | 11 |
| 30 | 14 | 31 | 5 | 32 | 6 | 33 | 8 |

In view of their ability to modulate the activity of the G-protein-coupled receptor GPR119, in particular an agonistic activity, the compounds of general formula I according to the invention, including the corresponding salts thereof, are suitable for the treatment of all those diseases or conditions which may be affected or which are mediated by the activation of the G-protein-coupled receptor GPR119.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the activation of the G-protein-coupled receptor GPR119 in a patient, preferably in a human.

In yet another aspect the present invention relates to a method for treating a disease or condition mediated by the activation of the G-protein-coupled receptor GPR119 in a mammal that includes the step of administering to a patient, preferably a human, in need of such treatment a therapeutically effective amount of a compound or a pharmaceutical composition of the present invention.

Diseases and conditions mediated by agonists of the G-protein-coupled receptor GPR119 embrace metabolic diseases or conditions.

According to one aspect the compounds and pharmaceutical compositions of the present invention are particularly suitable for treating diabetes mellitus, in particular Type 2 diabetes, Type 1 diabetes, complications of diabetes (such as e.g. retinopathy, nephropathy or neuropathies, diabetic foot, ulcers or macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia.

The compounds and pharmaceutical compositions of the present invention are also suitable for preventing beta-cell degeneration such as e.g. apoptosis or necrosis of pancreatic beta cells. The compounds and pharmaceutical compositions of the present invention are also suitable for improving or restoring the functionality of pancreatic cells, and also for increasing the number and size of pancreatic beta cells.

Therefore according to another aspect the invention relates to compounds of formula I and pharmaceutical compositions according to the invention for use in preventing, delaying, slowing the progression of and/or treating metabolic diseases, particularly in improving the glycaemic control and/or beta cell function in the patient.

In another aspect the invention relates to compounds of formula I and pharmaceutical compositions according to the invention for use in preventing, delaying, slowing the progression of and/or treating type 2 diabetes, overweight, obesity, complications of diabetes and associated pathological conditions.

In addition the compounds and pharmaceutical compositions according to the invention are suitable for use in one or more of the following therapeutic processes:

for preventing, delaying, slowing the progression of or treating metabolic diseases, such as for example type 1 diabetes, type 2 diabetes, insufficient glucose tolerance, insulin resistance, hyperglycaemia, hyperlipidaemia, hypercholesterolaemia, dyslipidaemia, syndrome X, metabolic syndrome, obesity, high blood pressure, chronic systemic inflammation, retinopathy, neuropathy, nephropathy, atherosclerosis, endothelial dysfunction or bone-related diseases (such as osteoporosis, rheumatoid arthritis or osteoarthritis);

for improving glycaemic control and/or reducing fasting plasma glucose, postprandial plasma glucose and/or the glycosylated haemoglobin HbA1c;

for preventing, delaying, slowing or reversing the progression of disrupted glucose tolerance, insulin resistance and/or metabolic syndrome to type 2 diabetes;

for preventing, delaying, slowing the progression of or treating a condition or a disease selected from among the complications of diabetes, such as for example retinopathy, nephropathy or neuropathies, diabetic foot, ulcers or macroangiopathies;

for reducing weight or preventing weight gain or assisting weight loss;

for preventing or treating the degradation of pancreatic beta cells and/or improving and/or restoring the functionality of pancreatic beta cells and/or restoring the functionality of pancreatic insulin secretion;

for maintaining and/or improving insulin sensitivity and/or preventing or treating hyperinsulinaemia and/or insulin resistance.

In particular, the compounds and pharmaceutical compositions according to the invention are suitable for the treatment of obesity, diabetes (comprising type 1 and type 2 diabetes, preferably type 2 diabetes mellitus) and/or complications of diabetes (such as for example retinopathy, nephropathy or neuropathies, diabetic foot, ulcers or macroangiopathies).

The compounds according to the invention are most particularly suitable for treating type 2 diabetes mellitus.

The dose range of the compounds of general formula I applicable per day is usually from 0.001 to 10 mg per kg body weight, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to one skilled in the art on the basis of his specialist knowledge. The preferred ones are those that are suitable for the particular formulation and method of administration that are desired. The preparations or formulations according to the invention may be prepared using methods known per se that are familiar to a person skilled in the art, such as for example by mixing or combining at least one compound of formula I according to the invention, or a pharmaceutically acceptable salt of such a compound, and one or more excipients, carriers and/or diluents.

Combination Therapy

The compounds of the invention may further be combined with one or more, preferably one, additional therapeutic agent. According to one embodiment, the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidaemia. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity and agents for the treatment of high blood pressure, heart failure and/or atherosclerosis.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset and 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors, bile acid-binding substances, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid) receptor, MCH-1 receptor antagonists, MC4 receptor agonists, NPY5 or NPY2 antagonists, β3-agonists, leptin or leptin mimetics and agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others. Combinations thereof are suitable. Angiotensin II receptor antagonists are preferably used for the treatment or prevention of high blood pressure and complications of diabetes, often combined with a diuretic such as hydrochlorothiazide.

The dosage for the combination partners mentioned above is usually ⅕ of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by the activation of the G-protein-coupled receptor GPR119, in particular diseases or conditions as described hereinbefore and hereinafter.

In yet another aspect the present invention relates a method for treating a disease or condition mediated by the activation of the G-protein-coupled receptor GPR119 in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

EXAMPLES

The terms "ambient temperature" and "room temperature" are used interchangeably and designate a temperature of about 20° C.

Preliminary Remarks:

As a rule, $^1$H-NMR and/or mass spectra have been obtained for the compounds prepared. The $R_f$ values are determined using Merck silica gel 60 $F_{254}$ plates and UV light at 254 nm.

Parameters of analytical HPLC employed for characterization of products (TFA denotes trifluoroacetic acid):

| Method: | 1 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [Methanol] | Flow [ml/min] | Temperature [° C.] |
| --- | --- | --- | --- | --- |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

| Method: | 2 |
| --- | --- |
| Device: | Agilent 1100 with DA and MS detector |
| Column: | XBridge C18, 4.6 × 30 mm, 3.5 μm |
| Column Supplier: | Waters |

| Gradient/ Solvent Time [min] | % Solvent [H$_2$O, 0.1% NH$_3$] | % Solvent [Methanol] | Flow [ml/min] | Temperature [° C.] |
| --- | --- | --- | --- | --- |
| 0.0 | 95 | 5 | 4 | 60 |
| 0.15 | 95 | 5 | 4 | 60 |
| 1.7 | 0 | 100 | 4 | 60 |
| 2.25 | 0 | 100 | 4 | 60 |

| Method: | 3 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [Acetonitrile] | Flow [ml/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 4 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% TFA] | % Solvent [Methanol] | Flow [ml/min] | Temperature [° C.] |
| --- | --- | --- | --- | --- |
| 0.0 | 95 | 5 | 1.9 | 60 |
| 0.20 | 95 | 5 | 1.9 | 60 |
| 1.55 | 0 | 100 | 1.9 | 60 |
| 1.60 | 0 | 100 | 2.4 | 60 |
| 1.80 | 0 | 100 | 2.4 | 60 |

| Method: | 5 |
| --- | --- |
| Device: | Agilent 1200 with DA and MS detector |
| Column: | XBridge C18, 3 × 30 mm, 2.5 μm |
| Column Supplier: | Waters |

| Gradient/ Solvent Time [min] | % Solvent [H$_2$O, 0.1% NH$_3$] | % Solvent [Acetonitrile] | Flow [ml/min] | Temperature [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Method: | 6 | | | |
|---|---|---|---|---|
| Device: | Agilent 1200 with DA and MS detector | | | |
| Column: | XBridge C18, 3 × 30 mm, 2.5 μm | | | |
| Column Supplier: | Waters | | | |
| Gradient/ Solvent Time [min] | % Solvent [$H_2O$, 0.1% $HCO_2H$] | % Solvent [Acetonitrile] | Flow [ml/min] | Temperature [° C.] |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Intermediate 1

5-Chloro-1''-tert-butoxycarbonyl-dispiro[2,3-dihydrofuro[2,3-c]pyridine-2,1'-cyclobutane-3',4''-piperidine]

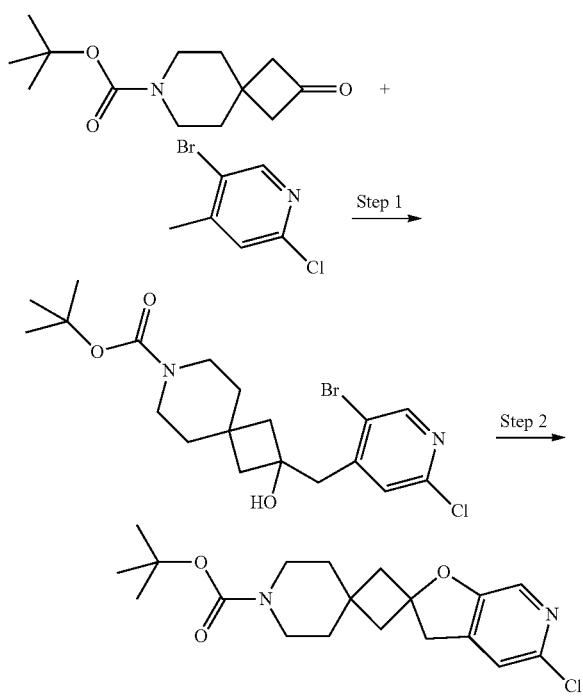

Step 1: 2-(5-bromo-2-chloro-pyridin-4-ylmethyl)-2-hydroxy-7-aza-spiro[3.5]nonane-7-carboxylic acid tert-butyl ester Lithium bis(trimethylsilyl)amide (1.0 mol/L in tetrahydrofuran; 8.0 mL) is added dropwise to 5-bromo-2-chloro-4-picoline (0.81 g) dissolved in tetrahydrofuran (10 mL) at −45° C. under Ar atmosphere. The solution is stirred at −35 to −45° C. for 0.5 h prior to dropwise addition of 2-oxo-7-aza-spiro[3.5]nonane-7-carboxylic acid tert-butyl ester (1.00 g) dissolved in tetrahydrofuran (5 mL). The reaction mixture is stirred at −40° C. for 45 min before the cooling bath is removed. At room temperature the reaction is quenched with aqueous $NH_4Cl$ solution and the resulting mixture is extracted with ethyl acetate. The combined extracts are dried ($Na_2SO_4$) and concentrated. The residue is chromatographed on silica gel (cyclohexane/ethyl acetate 4:1→1:1) to give the title compound. LC (method 1): $t_R$=1.36 min; Mass spectrum (ESI$^+$): m/z=445 [M+H]$^+$.

Step 2: 5-chloro-1''-tert-butoxycarbonyl-dispiro[2,3-dihydrofuro[2,3-c]pyridine-2,1'-cyclobutane-3',4''-piperidine]

A flask charged with a stir bar, 2-(5-bromo-2-chloro-pyridin-4-ylmethyl)-2-hydroxy-7-aza-spiro[3.5]nonane-7-carboxylic acid tert-butyl ester (1.50 g), racemic 2-(di-tert-butylphosphino)-1,1'-binaphthyl (0.27 g), cesium carbonate (1.65 g), and toluene (20 mL) is sparged with Ar for 10 min. Palladium acetate (0.15 g) is added and the mixture is heated to 85° C. and stirred at this temperature for 24 h. After cooling to room temperature, the mixture is concentrated and the residue is taken up in ethyl acetate and water. The resultant mixture is filtered over charcoal and the filtrate is concentrated. The residue is chromatographed on silica gel (cyclohexane/ethyl acetate 9:1→1:1) to give the title compound. LC (method 1): $t_R$=1.35 min; Mass spectrum (ESI$^+$): m/z=365/367 (Cl) [M+H]$^+$.

Intermediate 2

5-(4-Methylsulfonyl-phenyl)-dispiro[2,3-dihydrofuro[2,3-c]pyridine-2,1'-cyclobutane-3',4''-piperidine]

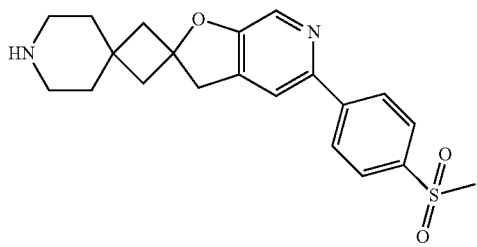 [SMILES: CS(=O)(=O)c1ccc(-c2cc3c(cn2)OC2(C3)CC3(CCNCC3)C2)cc1]

5-(4-Methylsulfonyl-phenyl)-1''-tert-butoxycarbonyl-dispiro[2,3-dihydrofuro[2,3-c]pyridine-2,1'-cyclobutane-3',4''-piperidine] (0.30 g) dissolved in 4 M HCl in 1,4-dioxane (5 mL) is stirred at room temperature for 1 h. The solution is diluted with 1,4-dioxane and concentrated to give the title compound as HCl salt. LC (method 1): $t_R$=0.66 min; Mass spectrum (ESI$^+$): m/z=385 [M+H]$^+$.

Intermediate 3

5-(1-Methanesulfonyl-1,2,3,6-tetrahydro-pyridin-4-yl)-dispiro[2,3-dihydrofuro[2,3-c]pyridine-2,1'-cyclobutane-3',4''-piperidine]

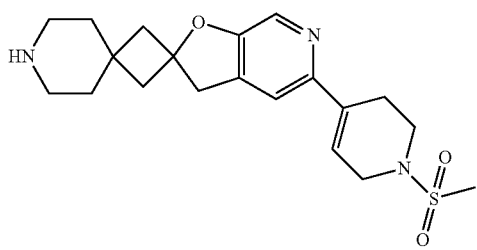 [SMILES: CS(=O)(=O)N1CC=C(c2cc3c(cn2)OC2(C3)CC3(CCNCC3)C2)CC1]

The title compound is prepared from 5-(1-methanesulfonyl-1,2,3,6-tetrahydro-pyridin-4-yl)-1"-tert-butoxycarbonyl-dispiro[2,3-dihydrofuro[2,3-c]pyridine-2,1'-cyclobutane-3',4"-piperidine] following a procedure analogous to that described for Intermediate 2; the compound is isolated as HCl salt. LC (method 1): $t_R$=0.51 min; Mass spectrum (ESI$^+$): m/z=390 [M+H]$^+$.

Intermediate 4

1"-(2-Hydroxy-2-methyl-propyl)-5-(4-methylsulfonyl-phenyl)-dispiro[2,3-dihydrofuro[2,3-c]pyridine-2,1'-cyclobutane-3',4"-piperidine]

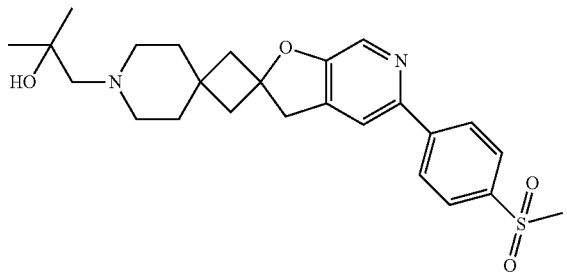 [SMILES: CC(C)(O)CN1CCC2(CC1)CC1(Cc3cc(-c4ccc(S(C)(=O)=O)cc4)ncc3O1)C2]

A mixture of 5-(4-methylsulfonyl-phenyl)-dispiro[2,3-dihydrofuro[2,3-c]pyridine-2,1'-cyclobutane-3',4"-piperidine] (HCl salt; 50 mg) and K$_2$CO$_3$ (17 mg) in methanol (4 mL) is stirred at room temperature for 15 min prior to the addition of isobutylene oxide (20 μL). The reaction vessel is sealed and the mixture is stirred at 60° C. overnight. After cooling to room temperature, the mixture is concentrated and the residue is chromatographed on silica gel (cyclohexane/ethyl acetate/methanol 5:4:1→0:9:1) to give the title compound. LC (method 1): $t_R$=0.71 min; Mass spectrum (ESI$^+$): m/z=457 [M+H]$^+$.

Intermediate 5

1"-Cyano-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine]

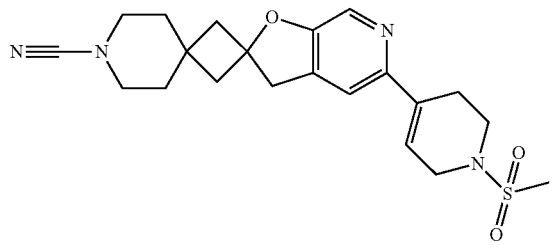 [SMILES: CS(=O)(=O)N1CC=C(c2cc3c(cn2)OC2(C3)CC3(CCN(C#N)CC3)C2)CC1]

A mixture of 5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (HCl salt, 0.22 g) and N,N-diisopropyl-ethylamine (0.22 mL) in dichloromethane (20 mL) is stirred at room temperature for 5 min. Bromocyanide (60 mg) is added and the solution is stirred at room temperature for 2 h. Water is added and the mixture is extracted with dichloromethane. The combined extracts are dried (Na$_2$SO$_4$) and concentrated. The residue is chromatographed on silica gel (cyclohexane/ethyl acetate/methanol 5:5:0→5:4:1) to give the title compound. Mass spectrum (ESI$^+$): m/z=415 [M+H]$^+$.

Intermediate 6

1"-(Hydroxy-carbaimidoyl)-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine]

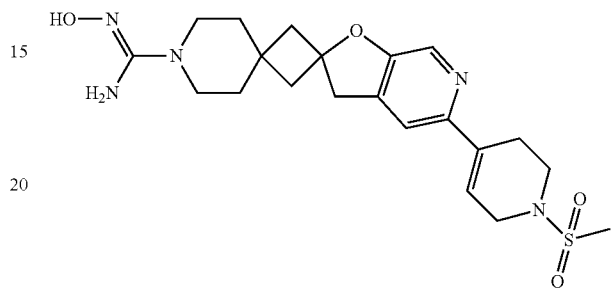

A mixture of 1"-cyano-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (365 mg), HONH$_2$*HCl (70 mg), triethylamine (0.15 mL), and ethanol (20 mL) is stirred at 65° C. for 3 h. After cooling to room temperature, the mixture is concentrated and the residue is chromatographed on silica gel (ethyl acetate/methanol 9:1→7:3) to give the title compound. Mass spectrum (ESI$^+$): m/z=448 [M+H]$^+$.

Example 1

5-(4-Methylsulfonyl-phenyl)-1"-tert-butoxycarbonyl-dispiro[2,3-dihydrofuro[2,3-c]pyridine-2,1'-cyclobutane-3',4"-piperidine]

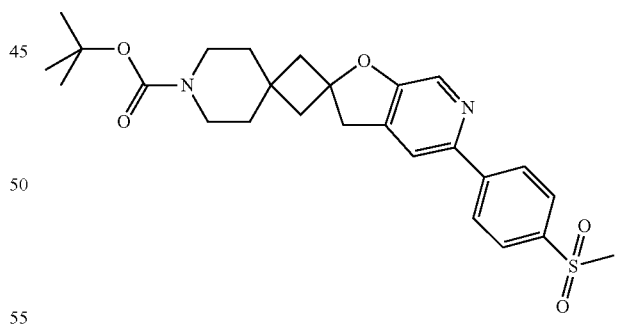

2 M aqueous Na$_2$CO$_3$ solution (0.30 mL) is added to a mixture of 5-chloro-1"-tert-butoxycarbonyl-dispiro[2,3-dihydrofuro[2,3-c]pyridine-2,1'-cyclobutane-3',4"-piperidine] (0.10 g), 4-(methanesulfonyl)phenylboronic acid (0.08 g), 1,4-dioxane (1.5 mL), and methanol (0.5 mL) at room temperature. The mixture is sparged with Ar for 10 min prior to addition of PdCl$_2$[1,1'-bis(diphenylphosphino)-ferrocene]*CH$_2$Cl$_2$ complex (20 mg). The resulting mixture is heated to reflux temperature and stirred at this temperature for 2 h. After cooling to room temperature, water and methanol are added and the resulting mixture is filtered. The filtrate is concentrated and the residue is chromatographed on reversed phase (HPLC, methanol/water) to give the title compound. LC (method 2): $t_R$=1.72 min; Mass spectrum (ESI⁺): m/z=485 [M+H]⁺.

Example 2

5-(1-Methanesulfonyl-1,2,3,6-tetrahydro-pyridin-4-yl)-1"-tert-butoxycarbonyl-dispiro[2,3-dihydrofuro[2,3-c]pyridine-2,1'-cyclobutane-3',4"-piperidine]

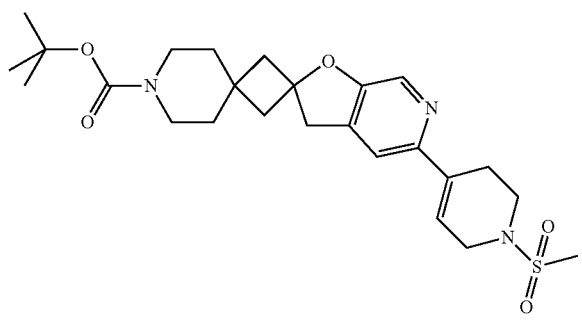 [SMILES: CC(C)(C)OC(=O)N1CCC2(CC1)CC1(Cc3cc(C4=CCN(S(C)(=O)=O)CC4)ncc3O1)C2]

A mixture of 5-chloro-1"-tert-butoxycarbonyl-dispiro[2,3-dihydrofuro[2,3-c]pyridine-2,1'-cyclobutane-3',4"-piperidine] (0.10 g), 1-methanesulfonyl-4-(4,4,5,5-tetramethyl-[1,3,2]dioxaborolan-2-yl)-1,2,3,6-tetrahydro-pyridine (0.10 g), 2 M aqueous Na₂CO₃ solution (0.37 mL), and 1,4-dioxane (2 mL) is sparged with argon for 10 min. Tetrakis(triphenylphosphine)palladium(0) (20 mg) is added and the mixture is stirred in a microwave oven at 150° C. for 1.5 h. After cooling to room temperature, water and methanol are added and the resulting mixture is filtered. The filtrate is concentrated and the residue is chromatographed on reversed phase (HPLC, methanol/water) to give the title compound. LC (method 2): $t_R$=1.63 min; Mass spectrum (ESI⁺): m/z=490 [M+H]⁺.

Example 3

5-(2-Fluoro-4-methylsulfonyl-phenyl)-1"-tert-butoxycarbonyl-dispiro[2,3-dihydrofuro[2,3-c]pyridine-2,1'-cyclobutane-3',4"-piperidine]

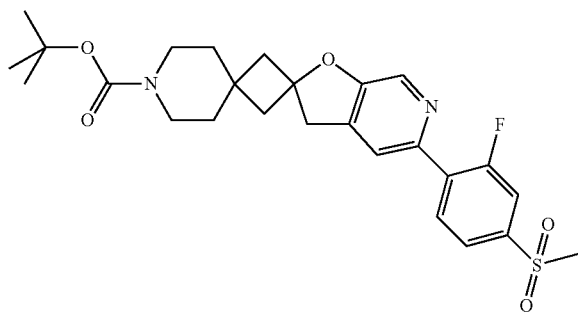 [SMILES: CC(C)(C)OC(=O)N1CCC2(CC1)CC1(Cc3cc(-c4ccc(S(C)(=O)=O)cc4F)ncc3O1)C2]

The title compound is prepared from 5-chloro-1"-tert-butoxycarbonyl-dispiro[2,3-dihydrofuro[2,3-c]pyridine-2,1'-cyclobutane-3',4"-piperidine] and 2-fluoro-4-methylsulfonyl-phenylboronic acid following a procedure analogous to that described for Example 2; PdCl₂[1,1'-bis(diphenylphosphino)-ferrocene]*CH₂Cl₂ complex is the preferred catalyst used. LC (method 1): $t_R$=1.30 min; Mass spectrum (ESI⁺): m/z=503 [M+H]⁺.

Example 4

1"-(5-Ethyl-pyrimidin-2-yl)-5-(4-methylsulfonyl-phenyl)-dispiro[2,3-dihydrofuro[2,3-c]pyridine-2,1'-cyclobutane-3',4"-piperidine]

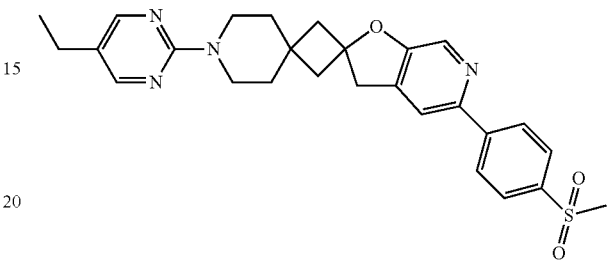

A mixture of 5-(4-methylsulfonyl-phenyl)-dispiro[2,3-dihydrofuro[2,3-c]pyridine-2,1'-cyclobutane-3',4"-piperidine] (HCl salt; 50 mg), 2-chloro-5-ethyl-pyrimidine (18 mg), potassium carbonate (35 mg), and N-methyl-pyrrolidinone (2 ml) is stirred at 80° C. for 4 h. After cooling to room temperature, water is added and the resulting mixture is extracted with ethyl acetate. The combined extracts are dried (Na₂SO₄) and concentrated. The residue is chromatographed on silica gel (cyclohexane/ethyl acetate 1:1→1:9) to give the title compound. LC (method 1): $t_R$=1.16 min; Mass spectrum (ESI⁺): m/z=491 [M+H]⁺.

Example 5

5-(4-Methylsulfonyl-phenyl)-1"-[(1-trifluoromethyl-cyclopropyl)-methyl]-dispiro[2,3-dihydrofuro[2,3-c]pyridine-2,1'-cyclobutane-3',4"-piperidine]

A solution of methanesulfonic acid (1-trifluoromethyl-cyclopropyl)methyl ester (45 mg) and sodium iodide (34 mg) in N,N-dimethylformamide (2 mL) is stirred at room temperature for 4 h. 5-(4-Methylsulfonyl-phenyl)-dispiro[2,3-dihydrofuro[2,3-c]pyridine-2,1'-cyclobutane-3',4"-piperidine] (HCl salt; 50 mg) and K₂CO₃ (35 mg) are added and the resulting mixture is heated to 60° C. After stirring the mixture at 60° C. for 4 h, water is added and the mixture is extracted with ethyl acetate. The combined extracts are dried (Na₂SO₄) and concentrated. The residue is triturated with methanol to give the title compound. LC (method 1): $t_R$=0.82 min; Mass spectrum (ESI$^+$): m/z=507 [M+H]$^+$.

Example 6

1"-(2-Fluoro-2-methyl-propyl)-5-(4-methylsulfonyl-phenyl)-dispiro[2,3-dihydrofuro[2,3-c]pyridine-2,1'-cyclobutane-3',4"-piperidine]

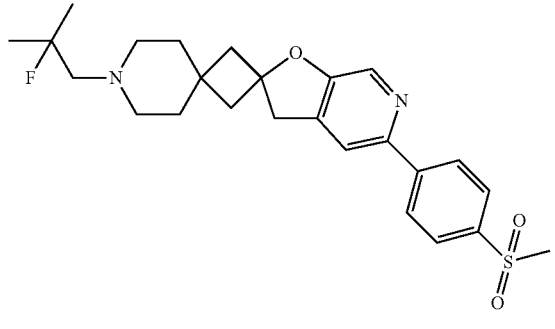 [SMILES: CC(C)(F)CN1CCC2(CC1)CC1(Cc3cc(-c4ccc(S(C)(=O)=O)cc4)ncc3O1)C2]

Bis(2-methoxyethyl)sulfur trifluoride (50% in toluene; 40 μL) is added to a solution of 1"-(2-hydroxy-2-methyl-propyl)-5-(4-methylsulfonyl-phenyl)-dispiro[2,3-dihydrofuro[2,3-c]pyridine-2,1'-cyclobutane-3',4"-piperidine] (20 mg) in dichloromethane (5 mL) chilled in an ice bath. The solution is stirred in the cooling bath for 2 h before another portion of bis(2-methoxyethyl)sulfur trifluoride (50% in toluene; 20 μL) is added. After stirring for 3 h, a few drops of methanol and water are added. The resulting solution is concentrated and the residue is purified by HPLC on reversed phase (acetonitrile/water/trifluoroacetic acid) to give the title compound as bis(trifluoroacetic acid) salt. LC (method 1): $t_R$=0.76 min; Mass spectrum (ESI$^+$): m/z=459 [M+H]$^+$.

Example 7

1"-(5-Methyl-pyrimidin-2-yl)-5-(4-methylsulfonyl-phenyl)-dispiro[2,3-dihydrofuro[2,3-c]pyridine-2,1'-cyclobutane-3',4"-piperidine]

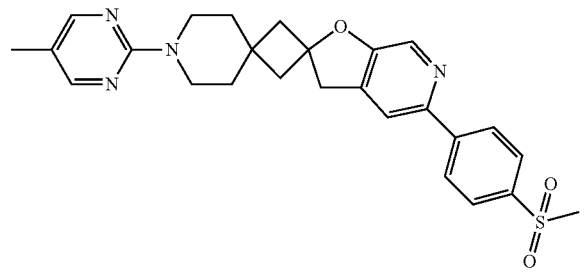

The title compound is prepared from 5-(4-methylsulfonyl-phenyl)-dispiro[2,3-dihydrofuro[2,3-c]pyridine-2,1'-cyclobutane-3',4"-piperidine] (HCl salt) and 2-bromo-5-methyl-pyrimidine following a procedure analogous to that described for Example 4. LC (method 1): $t_R$=1.07 min; Mass spectrum (ESI$^+$): m/z=477 [M+H]$^+$.

Example 8

5-(1-Methanesulfonyl-5-methyl-1,2,3,6-tetrahydro-pyridin-4-yl)-1"-tert-butoxycarbonyl-dispiro[2,3-dihydrofuro[2,3-c]pyridine-2,1'-cyclobutane-3',4"-piperidine]

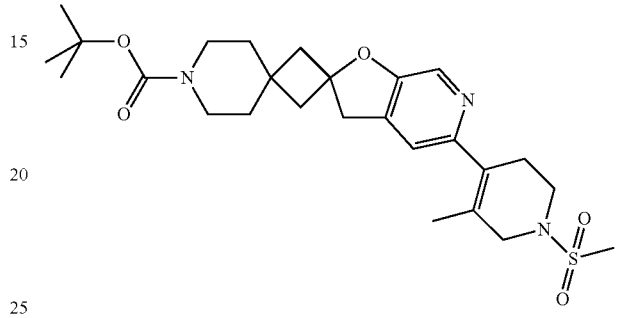

A flask is charged in air with a stir bar, 5-(1-methanesulfonyl-1,2,3,6-tetrahydro-pyridin-4-yl)-1"-tert-butoxycarbonyl-dispiro[2,3-dihydrofuro[2,3-c]pyridine-2,1'-cyclobutane-3',4"-piperidine] (50 mg), methylboronic acid (20 mg), Ag$_2$O (25 mg), 2-methylbutan-2-ol (1 mL), palladium(II) acetate (4 mg), and p-benzoquinone (6 mg). The flask is sealed and the mixture is heated to 105° C. After stirring at 105° C. for 2 h, the mixture is cooled to room temperature, diluted with dichloromethane/methanol (4:1), and filtered over Celite. The filtrate is concentrated and the residue is purified by HPLC on reversed phase (acetonitrile/water/trifluoroacetic acid) to give the title compound as trifluoroacetic acid salt. LC (method 1): $t_R$=1.08 min; Mass spectrum (ESI$^+$): m/z=504 [M+H]$^+$.

Example 9

1"-(5-Chloro-pyrimidin-2-yl)-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine]

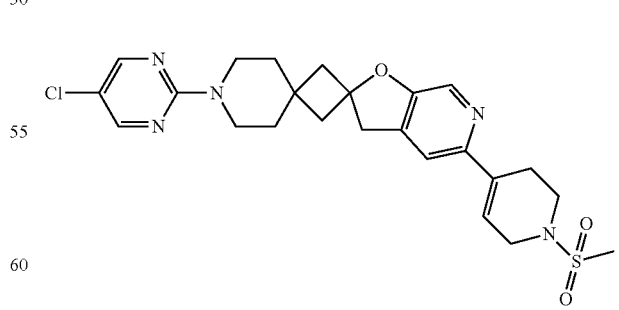

The title compound is prepared from 5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (HCl salt) and 2,5-dichloro-pyrimidine following a procedure analogous to that described for Example 4. LC (method 1): $t_R$=1.17 min; Mass spectrum (ESI⁺): m/z=502/504 (Cl) [M+H]⁺.

Example 10

1"-(Isopropyloxycarbonyl)-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine]

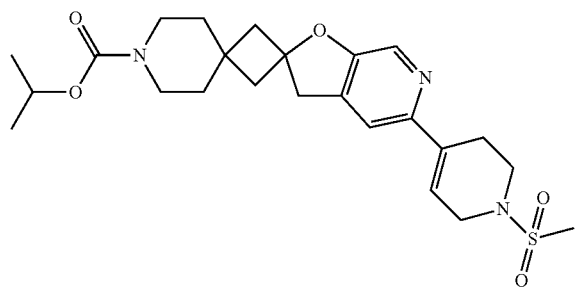 [SMILES: CC(C)OC(=O)N1CCC2(CC1)CC1(Cc3cc(C4=CCN(S(C)(=O)=O)CC4)ncc3O1)C2]

Isopropyl chloroformate (1 mol/L in toluene; 0.15 mL) is added to a mixture of 5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (HCl salt; 60 mg), triethylamine (40 µL), and dichloromethane (5 mL) at room temperature. The solution is stirred for 3 h and then concentrated. The residue is chromatographed on silica gel (cyclohexane/ethyl acetate 4:1→1:4) to give the title compound. LC (method 1): $t_R$=1.02 min; Mass spectrum (ESI⁺): m/z=476 [M+H]⁺.

Example 11

5-(1-Methanesulfonyl-1,2,3,6-tetrahydro-pyridin-4-yl)-1"-(5-trifluoromethyl-pyridin-2-yl)-dispiro[2,3-dihydrofuro[2,3-c]pyridine-2,1'-cyclobutane-3',4"-piperidine]

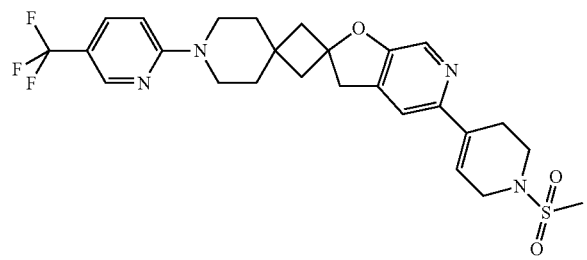

The title compound is prepared from 5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (HCl salt) and 2-chloro-5-trifluoromethyl-pyridine following a procedure analogous to that described for Example 4. LC (method 1): $t_R$=1.09 min; Mass spectrum (ESI⁺): m/z=535 [M+H]⁺.

Example 12

5-(1-Methanesulfonyl-1,2,3,6-tetrahydro-pyridin-4-yl)-1"-(1-methyl-cyclopropyloxycarbonyl)-dispiro[2,3-dihydrofuro[2,3-c]pyridine-2,1'-cyclobutane-3',4"-piperidine]

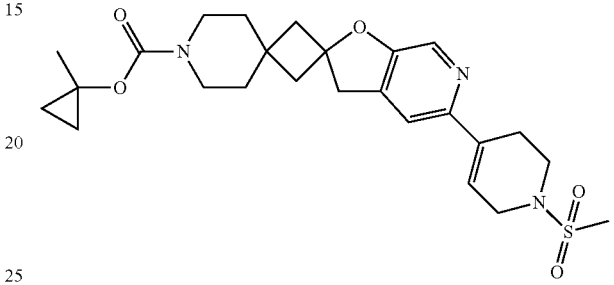

1-Methylcyclopropyl 4-nitro-phenyl carbonate (58 mg) is added to a mixture of 5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (HCl salt; 66 mg), triethylamine (65 µL), and tetrahydrofuran (5 mL) at room temperature. The solution is stirred at 60° C. overnight. Water is added and the resulting mixture is extracted with ethyl acetate. The combined extracts are dried (Na₂SO₄) and concentrated. The residue is chromatographed on silica gel (cyclohexane/ethyl acetate 4:1→1:4) to give the title compound. LC (method 1): $t_R$=1.02 min; Mass spectrum (ESI⁺): m/z=488 [M+H]⁺.

Example 13

5-(6-Methanesulfonyl-pyridin-3-yl)-1"-tert-butoxycarbonyl-dispiro[2,3-dihydrofuro[2,3-c]pyridine-2,1'-cyclobutane-3',4"-piperidine]

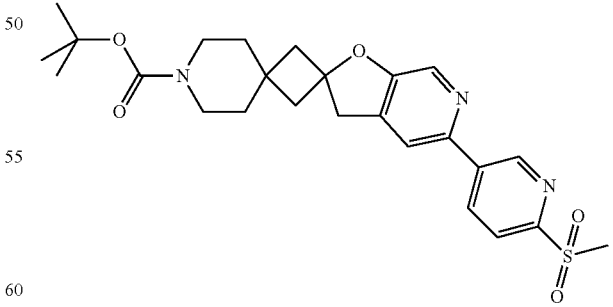

The title compound is prepared from 5-chloro-1"-tert-butoxycarbonyl-dispiro[2,3-dihydrofuro[2,3-c]pyridine-2,1'-cyclobutane-3',4"-piperidine] and 6-methylsulfonyl-pyridine-3-boronic acid pinacol ester following a procedure analogous to that described for Example 1; the reaction is conducted in a microwave oven at 140° C. LC (method 3): t_R=1.07 min; Mass spectrum (ESI+): m/z=486 [M+H]+.

Example 14

5-(4-Cyano-2-fluoro-phenyl)-1''-tert-butoxycarbonyl-dispiro[2,3-dihydrofuro[2,3-c]pyridine-2,1'-cyclobutane-3',4''-piperidine]

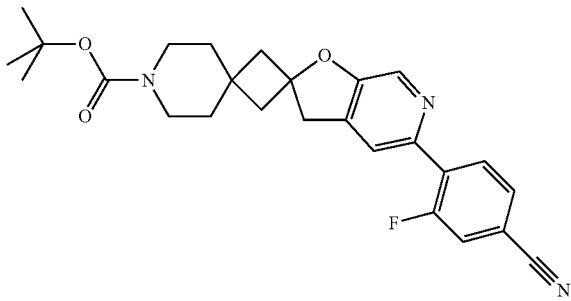 [SMILES: CC(C)(C)OC(=O)N1CCC2(CC1)CC1(Cc3cc(-c4ccc(C#N)cc4F)ncc3O1)C2]

The title compound is prepared from 5-chloro-1''-tert-butoxycarbonyl-dispiro[2,3-dihydrofuro[2,3-c]pyridine-2,1'-cyclobutane-3',4''-piperidine] and 4-cyano-2-fluoro-phenyl-boronic acid following a procedure analogous to that described for Example 1; the reaction is conducted in a microwave oven at 140° C. LC (method 3): t_R=1.16 min; Mass spectrum (ESI+): m/z=450 [M+H]+.

Example 15

1''-(5-Isopropoxy-pyrimidin-2-yl)-5-(1-methanesulfonyl-1,2,3,6-tetrahydro-pyridin-4-yl)-dispiro[2,3-dihydrofuro[2,3-c]pyridine-2,1'-cyclobutane-3',4''-piperidine]

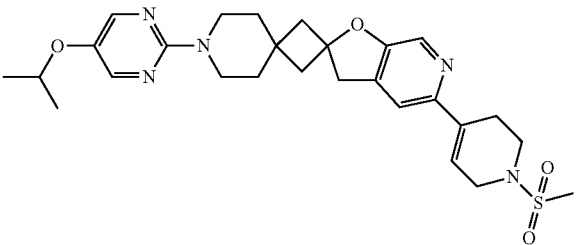 [SMILES: CC(C)Oc1cnc(N2CCC3(CC2)CC2(Cc4cc(C5=CCN(S(C)(=O)=O)CC5)ncc4O2)C3)nc1]

A mixture of 5-(1-methanesulfonyl-1,2,3,6-tetrahydro-pyridin-4-yl)-dispiro[2,3-dihydrofuro[2,3-c]pyridine-2,1'-cyclobutane-3',4''-piperidine] (HCl salt; 60 mg), 2-chloro-5-isopropoxy-pyrimidine (25 mg), potassium carbonate (45 mg), and N-methyl-pyrrolidinone (2 ml) is stirred in a microwave oven at 150° C. for 20 min. After cooling to room temperature, water is added and the resulting mixture is extracted with ethyl acetate. The combined extracts are dried (Na_2SO_4) and concentrated. The residue is chromatographed on silica gel (cyclohexane/ethyl acetate/methanol 5:5:0→5:5:1) to give the title compound. LC (method 3): t_R=0.93 min; Mass spectrum (ESI+): m/z=526 [M+H]+.

Example 16

5-(1-Methanesulfonyl-1,2,3,6-tetrahydro-pyridin-4-yl)-1''-(5-n-propyl-pyrimidin-2-yl)-dispiro[2,3-dihydrofuro[2,3-c]pyridine-2,1'-cyclobutane-3',4''-piperidine]

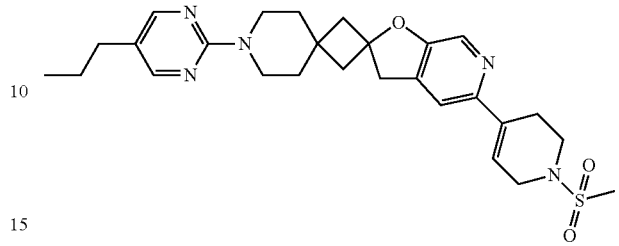

The title compound is prepared from 5-(1-methanesulfonyl-1,2,3,6-tetrahydro-pyridin-4-yl)-dispiro[2,3-dihydrofuro[2,3-c]pyridine-2,1'-cyclobutane-3',4''-piperidine] (HCl salt) and 2-chloro-5-n-propyl-pyrimidine following a procedure analogous to that described for Example 15. LC (method 3): t_R=0.88 min; Mass spectrum (ESI+): m/z=510 [M+H]+.

Example 17

1''-(5-Cyclopropyl-pyrimidin-2-yl)-5-(1-methanesulfonyl-1,2,3,6-tetrahydro-pyridin-4-yl)-dispiro[2,3-dihydrofuro[2,3-c]pyridine-2,1'-cyclobutane-3',4''-piperidine]

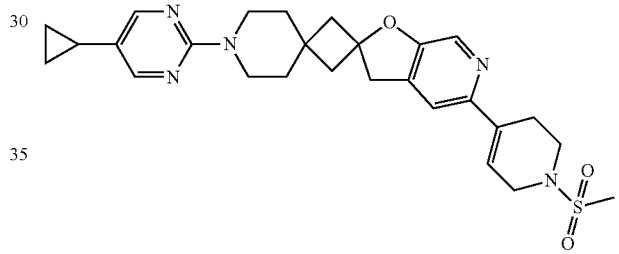

The title compound is prepared from 5-(1-methanesulfonyl-1,2,3,6-tetrahydro-pyridin-4-yl)-dispiro[2,3-dihydrofuro[2,3-c]pyridine-2,1'-cyclobutane-3',4''-piperidine] (HCl salt) and 2-chloro-5-cyclopropyl-pyrimidine following a procedure analogous to that described for Example 15. LC (method 3): t_R=0.85 min; Mass spectrum (ESI+): m/z=508 [M+H]+.

Example 18

5-(4-Methylsulfonylmethyl-phenyl)-1''-tert-butoxycarbonyl-dispiro[2,3-dihydrofuro[2,3-c]pyridine-2,1'-cyclobutane-3',4''-piperidine]

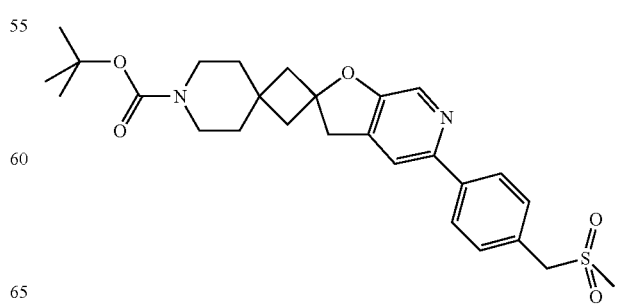

The title compound is prepared from 5-chloro-1"-tert-butoxycarbonyl-dispiro[2,3-dihydrofuro[2,3-c]pyridine-2,1'-cyclobutane-3',4"-piperidine] and 4-methylsulfonylmethylphenylboronic acid following a procedure analogous to that described for Example 1; the reaction is conducted in a microwave oven at 140° C. LC (method 3): $t_R$=0.95 min; Mass spectrum (ESI$^+$): m/z=499 [M+H]$^+$.

Example 19

5-(1-Methanesulfonyl-piperidin-4-yl)-1"-tert-butoxycarbonyl-dispiro[2,3-dihydrofuro[2,3-c]pyridine-2,1'-cyclobutane-3',4"-piperidine]

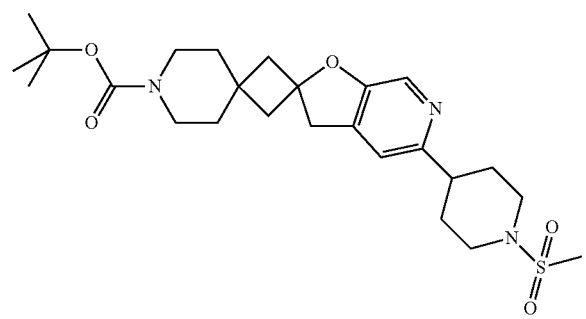 [SMILES: CC(C)(C)OC(=O)N1CCC2(CC1)CC1(Cc3cc(C4CCN(S(C)(=O)=O)CC4)ncc3O1)C2]

A flask charged with 5-(1-methanesulfonyl-1,2,3,6-tetrahydro-pyridin-4-yl)-1"-tert-butoxycarbonyl-dispiro[2,3-dihydrofuro[2,3-c]pyridine-2,1'-cyclobutane-3',4"-piperidine] (50 mg), 10% palladium on carbon (5 mg), and methanol (5 mL) is shaken under H$_2$ atmosphere (1 bar) at room temperature for 2 h. The catalyst is separated by filtration and the filtrate is concentrated to give the title compound. LC (method 3): $t_R$=0.93 min; Mass spectrum (ESI$^+$): m/z=492 [M+H]$^+$.

Example 20

5-(1-Methanesulfonyl-1,2,3,6-tetrahydro-pyridin-4-yl)-1"-(5-trifluoromethyl-[1,3,4]thiadiazol-2-yl)-dispiro[2,3-dihydrofuro[2,3-c]pyridine-2,1'-cyclobutane-3',4"-piperidine]

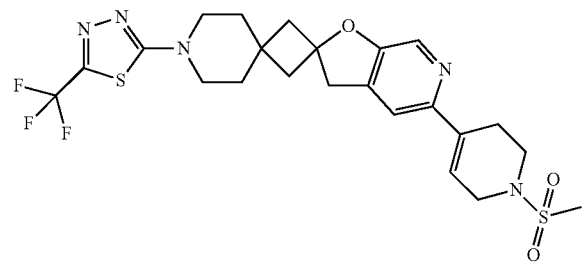 [SMILES: CS(=O)(=O)N1CC=C(c2cc3c(cn2)OC2(C3)CC3(CCN(c4nnc(C(F)(F)F)s4)CC3)C2)CC1]

The title compound is prepared from 5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (HCl salt) and 2-chloro-5-trifluoromethyl-[1,3,4]thiadiazole following a procedure analogous to that described for Example 15. LC (method 3): $t_R$=0.93 min; Mass spectrum (ESI$^+$): m/z=542 [M+H]$^+$.

Example 21

5-(4-Methanesulfonyl-piperazin-1-yl)-1"-tert-butoxycarbonyl-dispiro[2,3-dihydrofuro[2,3-c]pyridine-2,1'-cyclobutane-3',4"-piperidine]

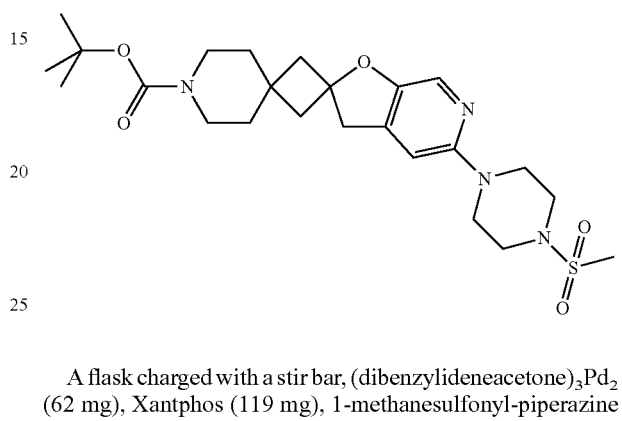

A flask charged with a stir bar, (dibenzylideneacetone)$_3$Pd$_2$ (62 mg), Xantphos (119 mg), 1-methanesulfonyl-piperazine (77 mg), KOtBu (93 mg), and toluene (5 mL) is sparged with Ar for 5 min. 5-Chloro-1"-tert-butoxycarbonyl-dispiro[2,3-dihydrofuro[2,3-c]pyridine-2,1'-cyclobutane-3',4"-piperidine] (100 mg) is added and the mixture is heated to 110° C. After stirring at 110° C. for 3 h, the mixture is cooled to room temperature and water is added. The resulting mixture is extracted with ethyl acetate and the combined extracts are concentrated. The residue is chromatographed on silica gel (cyclohexane/ethyl acetate/methanol 1:1:0-4:5:1) to give the title compound. LC (method 3): $t_R$=0.93 min; Mass spectrum (ESI$^+$): m/z=493 [M+H]$^+$.

Example 22

5-(4-Ethylaminocarbonyl-phenyl)-1"-tert-butoxycarbonyl-dispiro[2,3-dihydrofuro[2,3-c]pyridine-2,1'-cyclobutane-3',4"-piperidine]

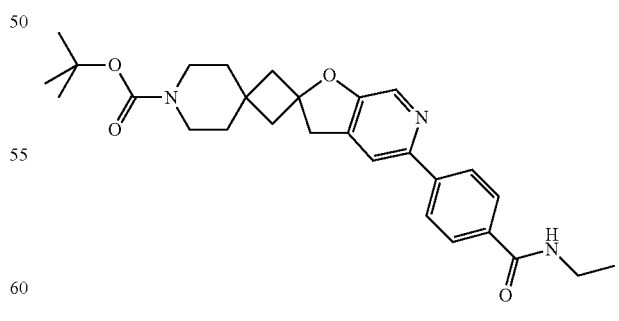

The title compound is prepared from 5-chloro-1"-tert-butoxycarbonyl-dispiro[2,3-dihydrofuro[2,3-c]pyridine-2,1'-cyclobutane-3',4"-piperidine] and 4-ethylaminocarbonyl-phenylboronic acid following a procedure analogous to that described for Example 1; the reaction is conducted in a microwave oven at 140° C. LC (method 3): $t_R$=1.26 min; Mass spectrum (ESI⁺): m/z=478 [M+H]⁺.

Example 23

1"-(3-Isopropyl-[1,2,4]oxadiazol-5-yl)-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine]

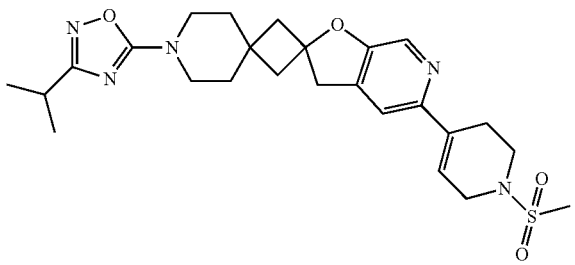 [SMILES: CC(C)c1noc(N2CCC3(CC2)CC2(Cc4cc(C5=CCN(S(C)(=O)=O)CC5)ncc4O2)C3)n1]

Zinc chloride (0.7 mol/L in tetrahydrofuran, 0.42 mL) is added to a solution of N-hydroxy-isobutyramidine (30 mg) and 1"-cyano-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (100 mg) in tetrahydrofuran (4 mL) and ethyl acetate (4 mL) at room temperature. The solution is heated to 60° C. and stirred at this temperature for 2 h.

After cooling to room temperature, the solution is concentrated and the residue is taken up in a mixture of ethanol (4 mL) and acetic acid (2 mL). The mixture is heated to 85° C. and stirred at this temperature for 2 h. The mixture is cooled to room temperature and concentrated. Aqueous NaHCO₃ solution is added and the resulting mixture is extracted with ethyl acetate. The combined extracts are dried (Na₂SO₄) and concentrated. The residue is chromatographed on silica gel (cyclohexane/ethyl acetate/methanol 5:5:0→5:4:1) to give the title compound. LC (method 3): $t_R$=0.76 min; Mass spectrum (ESI⁺): m/z=500 [M+H]⁺.

Example 24

5-(1-Methanesulfonyl-1,2,3,6-tetrahydro-pyridin-4-yl)-1"-(3-n-propyl-[1,2,4]oxadiazol-5-yl)-dispiro[2,3-dihydrofuro[2,3-c]pyridine-2,1'-cyclobutane-3',4"-piperidine]

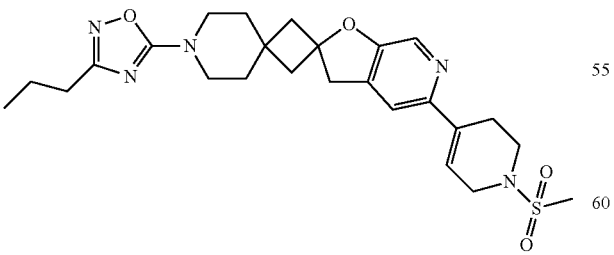

The title compound is prepared from N-hydroxy-butyramidine and 1"-cyano-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] following a procedure analogous to that described for Example 23. LC (method 3): $t_R$=0.91 min; Mass spectrum (ESI⁺): m/z=500 [M+H]⁺.

Example 25

1"-(5-Isopropyl-[1,2,4]oxadiazol-3-yl)-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine]

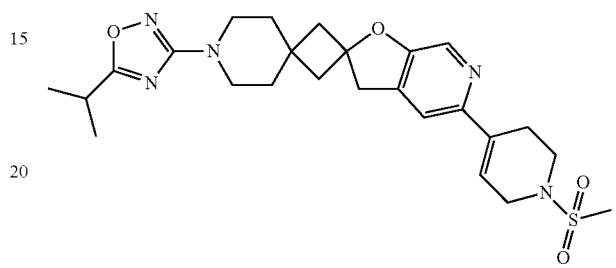

Isobutyryl chloride (10 µL) is added to a solution of 1"-(hydroxycarbamimidoyl)-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (40 mg) and triethylamine (41 µL) in tetrahydrofuran (3 mL) at room temperature. The solution is stirred at room temperature for 1 h and at 45° C. overnight. The solution is diluted with methanol and concentrated. The residue is chromatographed on silica gel (cyclohexane/ethyl acetate 3:7→1:9) to give the title compound. LC (method 4): $t_R$=1.13 min; Mass spectrum (ESI⁺): m/z=500 [M+H]⁺.

Example 26

5-(1-Methanesulfonyl-1,2,3,6-tetrahydro-pyridin-4-yl)-1"-(3-n-propyl-[1,2,4]oxadiazol-3-yl)-dispiro[2,3-dihydrofuro[2,3-c]pyridine-2,1'-cyclobutane-3',4"-piperidine]

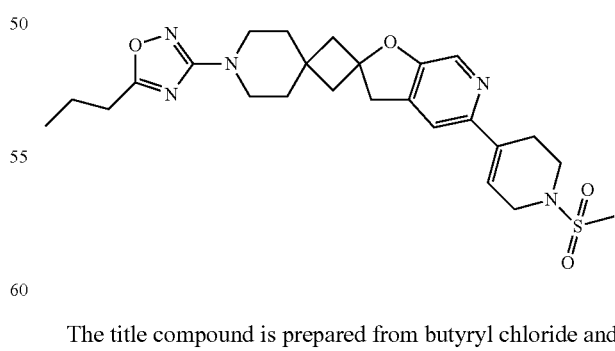

The title compound is prepared from butyryl chloride and 1"-(hydroxycarbamimidoyl)-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] following a procedure analogous to that described for Example 25. LC (method 3): $t_R$=0.93 min; Mass spectrum (ESI⁺): m/z=500 [M+H]⁺.

Example 27

1"-[(S)-2,2,2-Trifluoro-1-methyl-ethyloxycarbonyl]-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine]

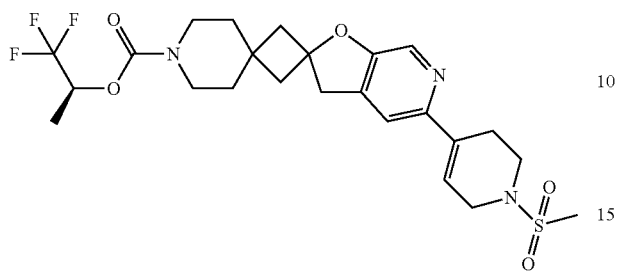

The title compound is prepared from 5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (HCl salt) and (S)-carbonic acid 4-nitro-phenyl ester 2,2,2-trifluoro-1-methyl-ethyl ester following a procedure analogous to that described for Example 12. LC (method 3): $t_R$=0.95 min; Mass spectrum (ESI$^+$): m/z=530 [M+H]$^+$.

Example 28

1"-(5-Ethyl-pyrimidin-2-yl)-5-(1-methanesulfonyl-1,2,3,6-tetrahydro-pyridin-4-yl)-dispiro[2,3-dihydrofuro[2,3-c]pyridine-2,1'-cyclobutane-3',4"-piperidine]

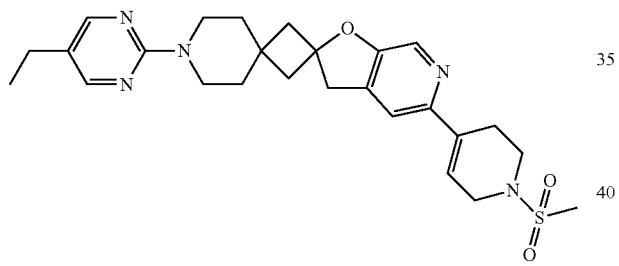

The title compound is prepared from 5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (HCl salt) and 2-chloro-5-ethyl-pyrimidine following a procedure analogous to that described for Example 15. LC (method 3): $t_R$=1.03 min; Mass spectrum (ESI$^+$): m/z=496 [M+H]$^+$.

Example 29

5-(4-Methylsulfanyl-phenyl)-1"-tert-butoxycarbonyl-dispiro[2,3-dihydrofuro[2,3-c]pyridine-2,1'-cyclobutane-3',4"-piperidine]

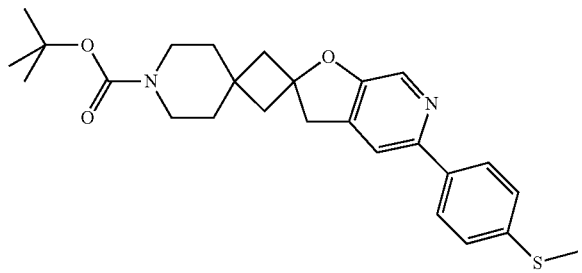 [SMILES: CSc1ccc(-c2cc3c(cn2)OC2(C3)CC3(CCN(C(=O)OC(C)(C)C)CC3)C2)cc1]

The title compound is prepared from 5-chloro-1"-tert-butoxycarbonyl-dispiro[2,3-dihydrofuro[2,3-c]pyridine-2,1'-cyclobutane-3',4"-piperidine] and 4-methylsulfanyl-phenyl-boronic acid following a procedure analogous to that described for Example 2; PdCl$_2$[1,1'-bis(diphenylphosphino)-ferrocene]*CH$_2$Cl$_2$ complex is used as catalyst source. LC (method 3): $t_R$=1.04 min; Mass spectrum (ESI$^+$): m/z=453 [M+H]$^+$.

Example 30

5-(2-Cyano-4-methylsulfanyl-phenyl)-1"-tert-butoxycarbonyl-dispiro[2,3-dihydrofuro[2,3-c]pyridine-2,1'-cyclobutane-3',4"-piperidine]

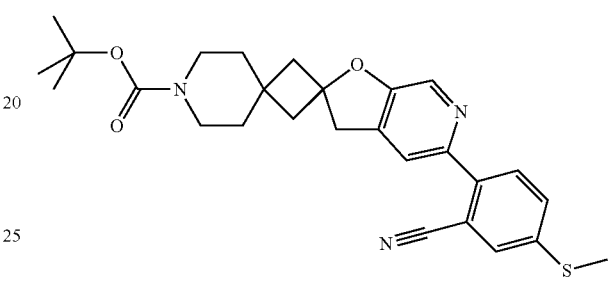

A mixture of 5-(4-methylsulfanyl-phenyl)-1"-tert-butoxycarbonyl-dispiro[2,3-dihydrofuro[2,3-c]pyridine-2,1'-cyclobutane-3',4"-piperidine] (100 mg), potassium cyanide (22 mg), copper(II) bromide (20 mg), palldium(II) acetate (5 mg), and N,N-dimethylformamide (5 mL) is stirred in air at 130° C. overnight. After cooling to room temperature, water is added and the mixture is extracted with ethyl acetate. The combined extract is dried (Na$_2$SO$_4$) and concentrated. The residue is chromatographed on silica gel (cyclohexane/ethyl acetate) to give the title compound. LC (method 3): $t_R$=1.17 min; Mass spectrum (ESI$^+$): m/z=478 [M+H]$^+$.

Example 31

5-(2-Cyano-4-methylsulfonyl-phenyl)-1"-tert-butoxycarbonyl-dispiro[2,3-dihydrofuro[2,3-c]pyridine-2,1'-cyclobutane-3',4"-piperidine]

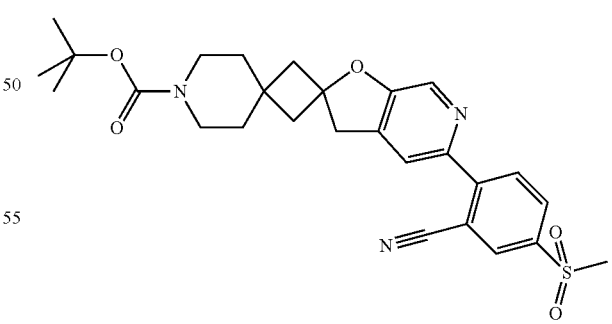

3-Chloroperbenzoic acid (75%, 88 mg) is added to a solution of 5-(2-cyano-4-methylsulfanyl-phenyl)-1"-tert-butoxycarbonyl-dispiro[2,3-dihydrofuro[2,3-c]pyridine-2,1'-cyclobutane-3',4"-piperidine] (80 mg) in dichloromethane (5 mL) chilled in an ice bath. The cooling bath is removed and the solution is stirred at room temperature overnight. Aqueous Na$_2$S$_2$O$_3$ solution and aqueous NaHCO$_3$ solution are

Example 32

5-(1-Methanesulfonyl-1,2,3,6-tetrahydro-pyridin-4-yl)-1"-(5-trifluoromethyl-pyrimidin-2-yl)-dispiro[2,3-dihydrofuro[2,3-c]pyridine-2,1'-cyclobutane-3',4"-piperidine]

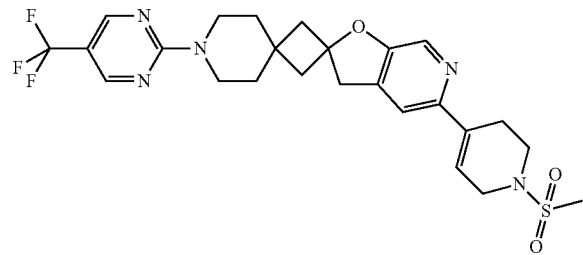 [SMILES: CS(=O)(=O)N1CC=C(c2cc3c(cn2)OC2(C3)CC3(CCN(c4ncc(C(F)(F)F)cn4)CC3)C2)CC1]

The title compound is prepared from 5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (HCl salt) and 2-chloro-5-trifluoromethyl-pyrimidine following a procedure analogous to that described for Example 15; the reaction is conducted at 45° C. overnight. LC (method 6): $t_R$=1.09 min; Mass spectrum (ESI$^+$): m/z=536 [M+H]$^+$.

Example 33

5-(1-Methanesulfonyl-1,2,3,6-tetrahydro-pyridin-4-yl)-1"-[(R)-2,2,2-trifluoro-1-methyl-ethyloxycarbonyl]-dispiro[2,3-dihydrofuro[2,3-c]pyridine-2,1'-cyclobutane-3',4"-piperidine]

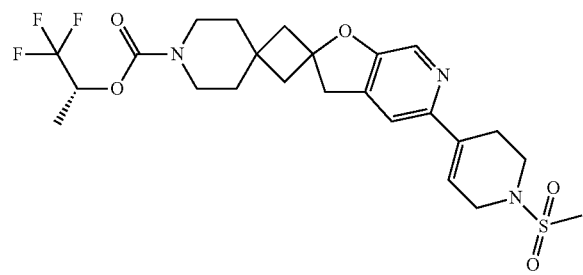 [SMILES: C[C@@H](OC(=O)N1CCC2(CC1)CC1(Cc3cc(C4=CCN(S(C)(=O)=O)CC4)ncc3O1)C2)C(F)(F)F]

The title compound is prepared from 5-(1-methanesulfonyl-1,2,3,6-tetrahydro-pyridin-4-yl)-dispiro[2,3-dihydrofuro[2,3-c]pyridine-2,1'-cyclobutane-3',4"-piperidine] (HCl salt) and (R)-carbonic acid 4-nitro-phenyl ester 2,2,2-trifluoro-1-methyl-ethyl ester following a procedure analogous to that described for Example 12. LC (method 6): $t_R$=1.00 min; Mass spectrum (ESI$^+$): m/z=530 [M+H]$^+$.

The invention claimed is:
1. A compound of formula I

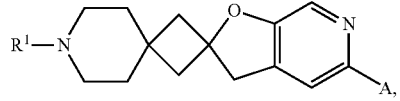

wherein:
$R^1$ is selected from the group $R^1$-G1 consisting of: (a) a 5- or 6-membered heteroaromatic ring containing 1, 2, or 3 heteroatoms independently selected from N, O, and S, optionally substituted with a group $R^C$ and/or one or more substituents independently selected from $L^A$, (b) a group C(=O)—O—$R^a$, wherein $R^a$ is $C_{1-6}$-alkyl optionally mono- or polysubstituted with fluorine, or $C_{3-6}$-cycloalkyl optionally mono- or polysubstituted with fluorine and optionally substituted with a group selected from $CH_3$, $CF_3$, and $CHF_2$; and (c) a group $CH_2$—$R^b$, wherein $R^b$ is $C_{1-6}$-alkyl optionally mono- or polysubstituted with fluorine, or $C_{3-6}$-cycloalkyl optionally mono- or polysubstituted with fluorine and optionally substituted with a group selected from $CH_3$, $CF_3$, and $CHF_2$;

A is selected from the group A-G1 consisting of: (a) piperidin-4-yl, 1,2,3,6-tetrahydropyridin-4-yl, 5-methyl-1,2,3,6-tetrahydro-pyridin-4-yl, and piperazin-1-yl, each substituted at the N with a $C_{1-4}$-alkyl-S(=O)$_2$— group; and (b) a phenyl ring and a 6-membered heteroaromatic ring containing 1 or 2 N, each optionally substituted with a group T and optionally substituted with one or more substituents independently selected from $L^A$;

T is selected from the group T-G1 consisting of F, Cl, Br, I, CN, OH, NO$_2$, $C_{1-6}$-alkyl-, $C_{1-6}$-alkenyl-, $C_{1-6}$-alkynyl-, $C_{3-6}$-cycloalkyl, $C_{1-6}$-alkyl-O—, $C_{3-6}$-cycloalkyl-O—, $C_{1-6}$-alkyl-S—, HO—C(=O)—, $C_{1-6}$-alkyl-O—C(=O)—, $C_{3-6}$-cycloalkyl-C(=O)—, $C_{1-4}$-alkyl-S(=O)—, $R^{NT1}R^{NT2}N$—, $R^{NT1}R^{NT2}N$—C(=O)—, $R^{NT1}R^{NT2}N$—S(=O)$_2$—, $R^{NT1}R^{NT2}N$—C(=O)—(R$^N$)N—, heterocyclyl, heterocyclyl-O—, aryl, aryl-O—, heteroaryl, and heteroaryl-O—, wherein each alkyl, alkenyl, alkynyl, and cycloalkyl group is optionally substituted with one or more substituents independently selected from F, Cl, CN, OH, $C_{1-3}$-alkyl, $C_{3-6}$-cycloalkyl, $C_{1-3}$-alkyl-O—, $R^{NT1}R^{NT2}N$—, $R^{NT1}R^{NT2}N$—C(=O)—, $C_{1-4}$-alkyl-S(=O)—, $C_{1-4}$-alkyl-S(=O)$_2$—, $R^{NT1}R^{NT2}N$—S(=O)$_2$—, aryl, heteroaryl, and heterocyclyl, and
wherein heteroaryl is a 5- or 6-membered aromatic ring which contains 1, 2, 3, or 4 heteroatoms independently selected from N, O, and S, wherein the H-atom in one or more NH groups are optionally replaced by $R^N$; and
wherein heterocyclyl is a 4- to 7-membered unsaturated or saturated carbocyclic ring in which 1, 2, or 3 —CH$_2$-groups are independently replaced by NR$^N$, O, —C(=O)—, S, —S(=O)—, or —S(=O)$_2$—, and/or in which a —CH< group is replaced by N;

$R^N$ is independently selected from the group $R^N$-G1 consisting of H, $C_{1-4}$-alkyl, $C_{1-4}$-alkyl-C(=O)—, and $C_{1-4}$-alkyl-S(=O)$_2$—;

$R^{NT1}$ is selected from the group $R^{NT1}$-G1 consisting of H, $C_{1-6}$-alkyl, $C_{3-6}$-cycloalkyl, $C_{1-6}$-alkyl-C(=O)—, $C_{1-6}$-alkyl-S(=O)$_2$, heterocyclyl, aryl, and heteroaryl, wherein each alkyl and cycloalkyl group is optionally substituted with one or more substituents independently selected from the group consisting of F, OH, CN, $C_{1-4}$-alkyl, $C_{1-4}$-alkyl-O—, $R^N_2N$, $C_{1-4}$-alkyl-S$(=O)_2$—, $C_{3-6}$-cycloalkyl, heterocyclyl, phenyl, and heteroaryl; and wherein heterocyclyl is optionally substituted with one or more substituents independently selected from F, $C_{1-4}$-alkyl, $R^N_2N$, OH, and $C_{1-4}$-alkyl-O—; and wherein heterocyclyl is a $C_{4-7}$-cycloalkyl ring in which 1 or 2 —$CH_2$-groups are independently replaced by $NR^N$, O, $C(=O)$, S, $S(=O)$ or $S(=O)_2$; and wherein heteroaryl is a 5- or 6-membered aromatic ring which contains 1, 2, or 3 heteroatoms independently selected from N, O, and S, wherein the H-atom in one or more NH groups is optionally replaced by $R^N$; and $R^{NT2}$ is selected from the group $R^{NT2}$-G1 consisting of H and $C_{1-6}$-alkyl; or $R^{NT1}$ and $R^{NT2}$ are linked to form one group selected from the group $R^{NT1}R^{NT2}$-G1 consisting of a $C_{3-5}$-alkylene group, wherein 1 or 2 —$CH_2$-groups are independently replaced by $NR^N$, O, $C(=O)$, S, $S(=O)$, or $S(=O)_2$; and are optionally substituted with one or more substituents independently selected from F, $(R^N)_2N$, OH, and $C_{1-4}$-alkyl-O—;

$L^A$ is selected from the group $L^A$-G1 consisting of F, Cl, Br, CN, OH, $NO_2$, $C_{1-4}$-alkyl-, $C_{1-4}$-alkyl-O—, $(R^N)_2N$—C$(=O)$, $(R^N)_2N$—, and $C_{1-4}$-alkyl-S$(=O)_2$—, wherein each alkyl group is optionally substituted with one or more substituents independently selected from F, Cl, CN, OH, and $C_{1-3}$-alkyl-O—; and $R^C$ is selected from the group $R^C$-G1 consisting of F, Cl, Br, I, CN, OH, $NO_2$, $C_{1-6}$-alkyl-, $C_{2-6}$-alkenyl-, $C_{2-6}$-alkynyl-, $C_{3-6}$-cycloalkyl, $C_{1-6}$-alkyl-O—, $C_{3-6}$-cycloalkyl-O—, $C_{1-6}$-alkyl-S—, HO—$C(=O)$—, $C_{1-6}$-alkyl-O—$C(=O)$—, $C_{3-6}$-cycloalkyl-$C(=O)$—, $C_{1-4}$-alkyl-S$(=O)$—, $R^{NT1}R^{NT2}N$—, $R^{NT1}R^{NT2}N$—$C(=O)$—, $R^{NT1}R^{NT2}N$—$S(=O)_2$—, $R^{NT1}R^{NT2}N$—$C(=O)$—$(R^N)N$—, heterocyclyl, heterocyclyl-O—, aryl, aryl-O—, heteroaryl, and heteroaryl-O—, wherein each alkyl, alkenyl, alkynyl, and cycloalkyl group is optionally substituted with one or more substituents independently selected from F, Cl, CN, OH, $C_{1-3}$-alkyl, $C_{3-6}$-cycloalkyl, $C_{1-3}$-alkyl-O—, $R^{NT1}R^{NT2}N$—, $R^{NT1}R^{NT2}N$—$C(=O)$—, $C_{1-4}$-alkyl-S$(=O)$—, $R^{NT1}R^{NT2}N$—$S(=O)_2$—, aryl, heteroaryl, and heterocyclyl, wherein heteroaryl is a 5- or 6-membered aromatic ring which contains 1, 2, 3, or 4 heteroatoms independently of each other selected from N, O and S, wherein the H-atom in one or more NH groups are optionally replaced by $R^N$; and wherein heterocyclyl is a 4- to 7-membered unsaturated or saturated carbocyclic ring in which 1, 2 or 3 —$CH_2$-groups independently of each other are replaced by $NR^N$, O, —$C(=O)$—, S, —$S(=O)$— or —$S(=O)_2$—, and/or in which a —CH-group is replaced by N; and wherein:

aryl is phenyl or naphthyl, and each aryl, heteroaryl, or heterocyclyl group is optionally substituted with one or more substituents independently selected from $L^A$, or a salt thereof.

2. The compound according to claim 1, wherein $R^1$ is selected from a group consisting of:

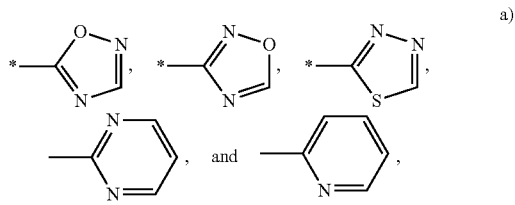

wherein each ring is optionally substituted with one substituent $R^C$;

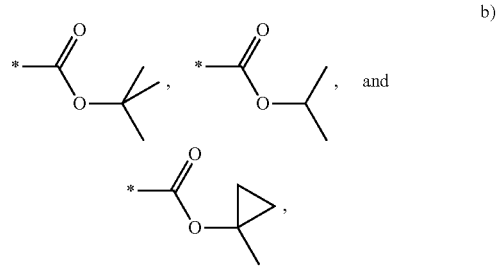

wherein each alkyl residue is substituted with 1 to 3 F atoms; and

3. The compound according to claim 1, wherein A is selected from a group consisting of:

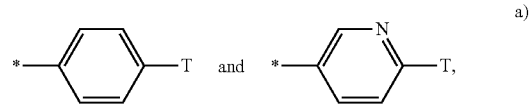

each optionally additionally substituted with one CN group or with one or two F atoms; and

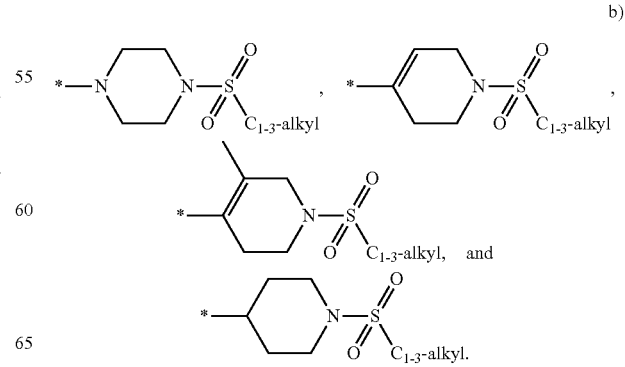

4. The compound according to claim 1, wherein T is selected from a group consisting of —CN, $C_{1\text{-}4}$-alkyl-S—, $C_{1\text{-}4}$-alkyl-S(=O)$_2$—CH$_2$—, $C_{1\text{-}4}$-alkyl-S(=O)$_2$, $R^{NT1}R^{NT2}$N—S(=O)$_2$—, $R^{NT1}R^{NT2}$N—C(=O)—, $C_{1\text{-}4}$-alkyl-S(=O)$_2$—(R$^N$)N—, and $R^{NT1}R^{NT2}$N—.

5. The compound according to claim 1, wherein $R^C$ is selected from a group consisting of F, Cl, Br, CN, $C_{1\text{-}4}$-alkyl-, $C_{3\text{-}6}$-cycloalkyl, $C_{1\text{-}4}$-alkyl-O—, $C_{3\text{-}6}$-cycloalkyl-O—, heterocyclyl, and heterocyclyl-O—, wherein each alkyl and cycloalkyl group is optionally substituted with one or more fluorine atoms and a substituent selected from H$_3$C— and H$_3$C—O—, and wherein heterocyclyl is selected from the group consisting of oxetanyl, tetrahydrofuranyl, and tetrahydropyranyl, each optionally substituted with one or two H$_3$C— groups.

6. The compound according to claim 1, wherein $R^1$ is selected from a group consisting of:

(a)

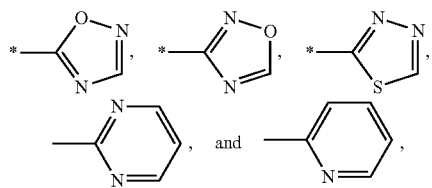

wherein each ring is optionally substituted with one substituent $R^C$;

(b)

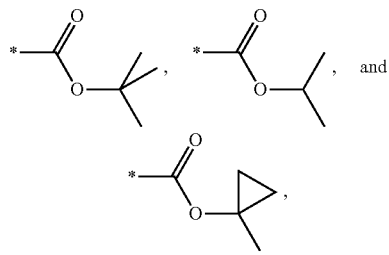

wherein each alkyl residue is optionally substituted with 1 to 3 F atoms; and (c)

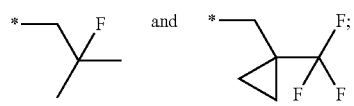

$R^C$ is selected from a group consisting of Cl, $C_{1\text{-}3}$-alkyl, cyclopropyl, F$_3$C—, and isopropyl-O—;

A is selected from a group consisting of:

(a)

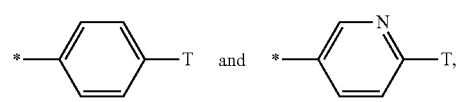

each of which is optionally additionally substituted with one CN group or with one or two F atoms; and (b)

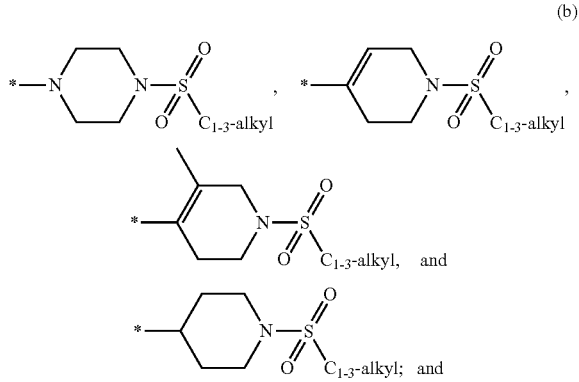

T is selected from a group consisting of NC—, CH$_3$—S—, CH$_3$—CH$_2$—NH—C(=O)—, CH$_3$—S(=O)$_2$—CH$_2$—, and CH$_3$—S(=O)$_2$—;

and the pharmaceutically acceptable salts thereof.

7. The compound according to claim 1, wherein:

$R^1$ is selected from a group consisting of

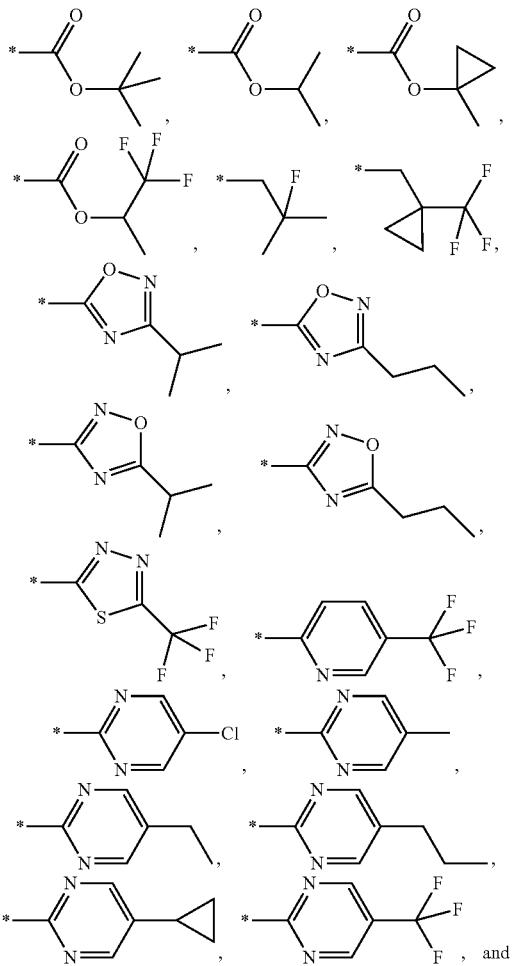

-continued

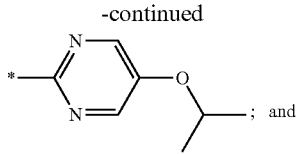
; and

A is selected from a group consisting of

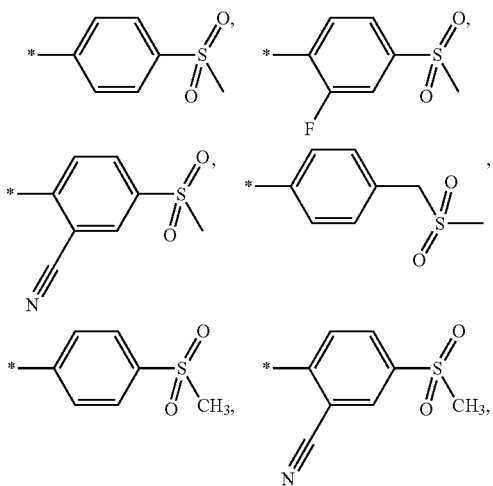

-continued

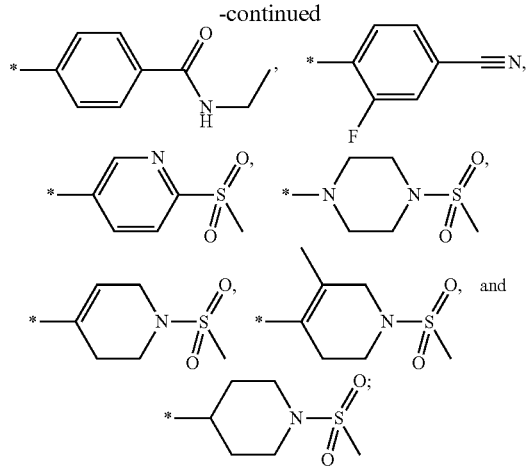

and the pharmaceutically acceptable salts thereof.

8. The pharmaceutically acceptable salt of a compound according to claim 1.

9. A pharmaceutical composition comprising the compound according to claim 1 or a pharmaceutically acceptable salt thereof, and an inert carrier or diluent.

10. A method for treating diabetes, obesity, or dyslipidemia in a patient in need thereof, comprising administering to the patient the compound according to claim 1 or a pharmaceutically acceptable salt thereof.

\* \* \* \* \*